US006911564B2

(12) United States Patent
Khachik

(10) Patent No.: US 6,911,564 B2
(45) Date of Patent: Jun. 28, 2005

(54) METHOD FOR PRODUCTION OF RARE CAROTENOIDS FROM COMMERCIALLY AVAILABLE LUTEIN

(75) Inventor: Frederick Khachik, Rockville, MD (US)

(73) Assignee: University of Maryland, College Park, College Park, MD (US)

( * ) Notice: Subject to any disclaimer, the term of this patent is extended or adjusted under 35 U.S.C. 154(b) by 167 days.

(21) Appl. No.: 10/333,724

(22) PCT Filed: Jul. 26, 2001

(86) PCT No.: PCT/US01/23422

§ 371 (c)(1),
(2), (4) Date: Jan. 24, 2003

(87) PCT Pub. No.: WO02/10128

PCT Pub. Date: Feb. 7, 2002

(65) Prior Publication Data

US 2003/0220525 A1 Nov. 27, 2003

Related U.S. Application Data

(60) Provisional application No. 60/220,995, filed on Jul. 27, 2000.

(51) Int. Cl.[7] ............................................. C07C 35/21
(52) U.S. Cl. ........................................................ 568/816
(58) Field of Search ................................ 568/816, 817

(56) References Cited

U.S. PATENT DOCUMENTS 4,235,820 A * 11/1980 Evans ......................... 564/379

FOREIGN PATENT DOCUMENTS

| GB | 1081104 | | 8/1967 |
| GB | 1081104 A | * | 9/1967 |
| WO | WO 99/20587 A1 | | 4/1999 |
| WO | WO 01/83414 A1 | | 11/2001 |

OTHER PUBLICATIONS

Khachik, J. Chromatogr. B, vol. 670, pp. 219–233 (1995).*
Zechmeistez, J. Am. Chem. Soc., vol. 65, pp. 1951–1965 (1943).*
Aidhen, Indian J. Chem., vol. 328 , pp. 231–238 (1993).*
Lau, J. Org. Chem., vol. 51, pp. 1038–3043 (1986).*
Dehmol, Synth. Commun. vol. 26, pp. 1467–1172 (1996).*
Wustrow, Tetrahedron Lett., vol. 35, pp. 61–64 (1994).*
Buchecker, Helv. Chim. Acta, vol. 57, pp 631–656 (1974).*
Aidhen, I.S., and Narasimhan, N.S., "A novel and versatile synthesis of 1–arylbenzocyclobutenols and 1–arylbenzocyclobutenes," *Ind. J. Chem. 32B*:234–238, Council of Scientific & Industrial Research (1993).

Buchecker, R., et al., "Absolute Konfiguration von Xanthophyll (Lutein)," *Helv. Chim. Acta* 57:631–656, Schweizerische Chemische Gesellschaft (1974), (no translation).
da S. Costa, J. et al., "Deoxygenation of Furanmethanols with $ZnI_2$–$NaCNBH_3$. An Efficient Protocol for the Preparation of 2– and 3–alkylfuran Compounds," *J. Braz. Chem. Soc.* 5:113–116, Sociedade Brasileira de Quimica (1994).
Dehmlow, E.V., et al., "Mild and Fast Deoxygenation of Aromatic Carbonyl Compounds by Diethylamine Borane/ Titanium Tetrachloride," *Synth. Commun.* 26:1467–1472, Marcel Dekker, Inc. (1996).
Goodfellow, D., et al., "The Absolute Configuration of Lutein," *J. Chem. Soc. Chem. Commun.* 13:1578, The Chemical Society (1978).
Isler, O., et al., "Synthesen in der Carotinoid–Reihe. Totalsynthese von Kryptoxanthin und eine weitere Synthese von Zeaxanthin," *Helv. Chim. Acta.* 40:456–467 Schweizerische Chemische Gesellschaft (1957), (no translation).
Khachik, F., et al., "Isolation, structural elucidation, and partial synthesis of lutein dehydration products in extracts from human plasma," *J. Chrom. B. Biomed. Appl.* 670:219–233, Elsevier Science B.V. (1995).
Lau, C.K. et al., "Reductive Deoxygenation of Aryl Aldehydes and Ketones and Benzylic, Allylic, and Tertiary Alcohols by $ZnI_2$–$NaCNBH_3$," *J. Org. Chem.* 51:3038–3043, American Chemical Society (1986).
Loeber, D.E., et al., "Carotenoids and Related Compounds. Part XXVIII. Synthesis of Zeaxanthin, β–Cryptoxanthin, and Zeinoxanthin (α–Cryptoxanthin)," *J. Chem. Soc. (C) Part 1*:404–408, The Chemical Society (1971).
Wustrow, D.J., et al., "Selective Deoxygenation of Allylic Alcohols and Acetates by Lithium Perchlorate Promoted Triethylsilane Reduction," *Tetrahedron Lett.* 35:61–64, Pergamon Press Ltd. (1994).
Zechmeister, L., and Sease, J.W., "Conversion of Lutein in a Boric Acid–Naphthalene Melt. I," *J. Am. Chem. Soc.* 65:1951–1955, American Chemical Society (1943).
International Search Report for International Application No. PCT/US01/23422, 3 pages, European Patent Office, Rijswijk, The Netherlands (mailed Mar. 19, 2002).

* cited by examiner

Primary Examiner—Michael L. Shippen
(74) Attorney, Agent, or Firm—Sterne, Kessler, Goldstein & Fox P.L.L.C.

(57) ABSTRACT

Disclosed are processes for conversion of (3R,3'R,6'R)-lutein to (3R,6'R)-α-cryptoxanthin, (3R)-β-cryptoxanthin, anhydroluteins I, II, and III (dehydration products of lutein), and a method for separating and purifying the individual carotenoids including the unreacted (3R,3'R)-zeaxanthin. The invention also includes two methods that transform (3R,3'R,6'R)-lutein into (3R,6'R)-α-cryptoxanthin in excellent yields.

52 Claims, No Drawings

METHOD FOR PRODUCTION OF RARE CAROTENOIDS FROM COMMERCIALLY AVAILABLE LUTEIN

BACKGROUND OF THE INVENTION

1. Field of the Invention

The invention is in the field of organic chemistry. The invention relates to an efficient process for conversion of commercially available (3R,3'R,6'R)-lutein containing 5–7% (3R,3'R)-zeaxanthin to (3R,6'R)-α-cryptoxanthin, (3R)-β-cryptoxanthin, anhydroluteins I, II, and III (dehydration products of lutein), and a method for separating and purifying the individual carotenoids including the unreacted (3R,3'R)-zeaxanthin. The invention also includes two methods that transform (3R,3'R,6'R)-lutein into (3R,6'R)-α-cryptoxanthin in excellent yields.

2. Related Art (3R,6'R)-α-Cryptoxanthin, (3R)-β-cryptoxanthin, (3R,6'R)-anhydrolutein I ((3R,6'R)-3',4'-didehydro-β,γ-caroten-3-ol), (3R,6'R)-2',3'-anhydrolutein II ((3R,6'R)-2',3'-didehydro-β,ε-caroten-3-ol), (3R)-3',4'-anhydrolutein III ((3R)-3',4'-didehydro-β,β-caroten-3-ol), and (3R,3'R)-zeaxanthin are among the major dietary carotenoids that are found in human serum, milk, major organs, and tissues. The chemical structures of these carotenoids are shown in Scheme 1. In view of the biological activity of carotenoids in the prevention of chronic diseases such as cancer, age-related macular degeneration, and cardiovascular disease, industrial production of a wide range of purified carotenoids is of great importance. While several dietary carotenoids, i.e. β-carotene, (3R,3'R,6'R)-lutein, and lycopene, are commercially available in various formulations as nutritional supplements and food coloring additives, the production of other serum carotenoids has not yet received much attention. In particular, (3R,6'R)-α-cryptoxanthin and (3R)-β-cryptoxanthin are among the rare carotenoids in nature and as a result extraction and isolation of these carotenoids from natural products on industrial scale is not economically viable.

SCHEME 1.

The chemical structures of (3R,3'R,6'R)-lutein, (3R,3'R)-zeaxanthin, anhydroluteins I, II, III, (3R,6'R)-α-cryptoxanthin, and (3R)-β-cryptoxanthin. The trivial and the correct systematic names for carotenoids are shown below their structures.

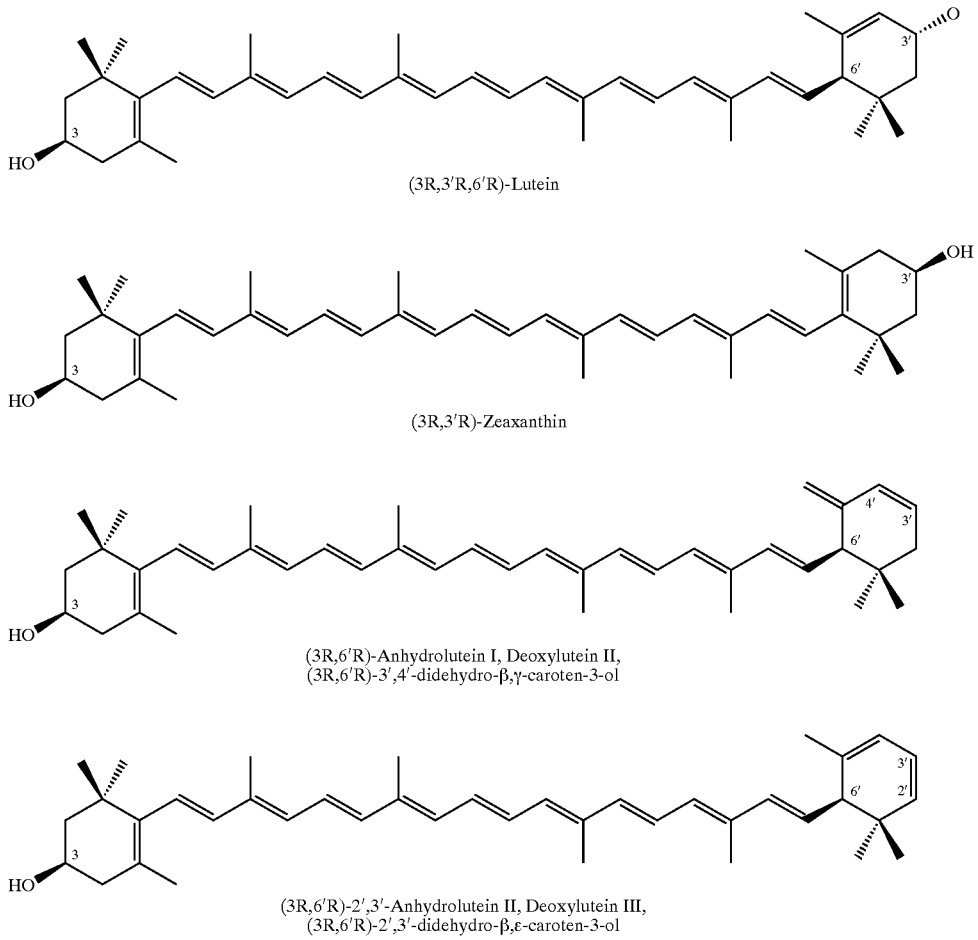

(3R,3'R,6'R)-Lutein (3R,3'R)-Zeaxanthin (3R,6'R)-Anhydrolutein I, Deoxylutein II,
(3R,6'R)-3',4'-didehydro-β,γ-caroten-3-ol (3R,6'R)-2',3'-Anhydrolutein II, Deoxylutein III,
(3R,6'R)-2',3'-didehydro-β,ε-caroten-3-ol

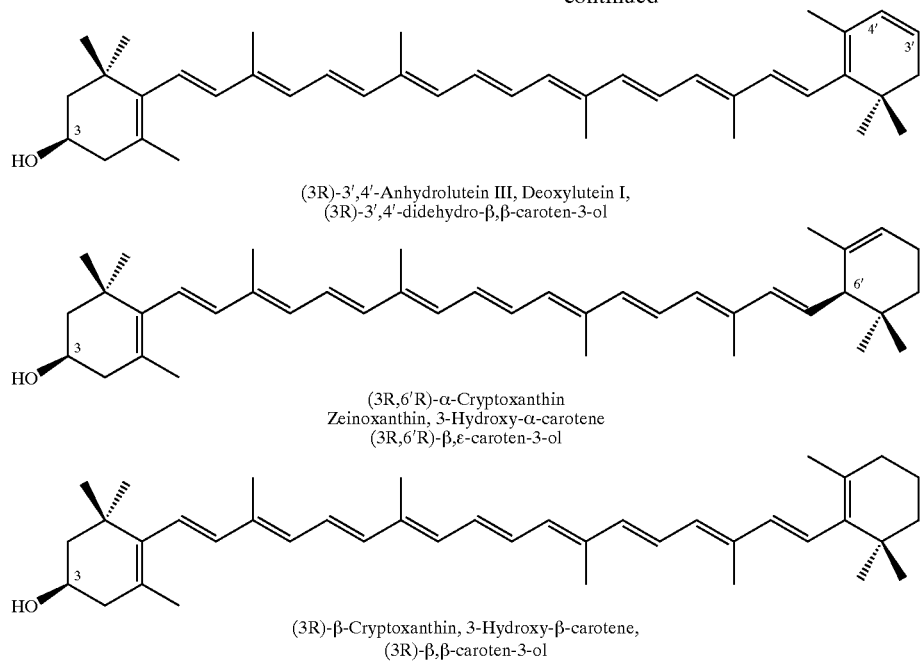

(3R)-3',4'-Anhydrolutein III, Deoxylutein I,
(3R)-3',4'-didehydro-β,β-caroten-3-ol (3R,6'R)-α-Cryptoxanthin
Zeinoxanthin, 3-Hydroxy-α-carotene
(3R,6'R)-β,ε-caroten-3-ol (3R)-β-Cryptoxanthin, 3-Hydroxy-β-carotene,
(3R)-β,β-caroten-3-ol Meanwhile, the natural occurrence of anhydroluteins I, II, and III is uncertain. These carotenoids are presumably formed from acid-catalyzed dehydration of dietary (3R,3'R,6'R)-lutein in the human digestive system.

The total syntheses of (3R,6'R,)-α-cryptoxanthin and (3R)-β-cryptoxanthin has been reported by several researchers (Isler, O. et al. *Helv. Chim. Acta*, 40:456, 1957; Loeber, D. E. et al. *J. Chem. Soc.* (C) 404, 1971). These synthetic methods involve numerous steps and are therefore quite costly and difficult to implement on industrial scale, (3R, 6'R)-α-Cryptoxanthin has also been prepared by partial synthesis from lutein (Goodfellow at al., *Chem. Comm.* 1578, 1970). According to this procedure, lutein is first treated with pyridine-sulfur trioxide complex, and the resulting sulfate monoester is reduced with lithium aluminum hydride (LAH) to give (3R,6'R)-α-cryptoxanthin; the yield and the details of the reaction conditions were not provided. The application of this method to industrial production of (3R,6'R)-α-cryptoxanthin is not readily feasible because of the sensitivity of the reagents to air and moisture. Another difficulty is due to the fact that LAH reduction of carotenoids has to be conducted under controlled conditions to avoid degradation of the starting material and the formation of side products. In addition, this process does not appear to be suitable for the preparation of (3R)-β-cryptoxanthin.

There are several reports on the partial synthesis of (3R,6'R)-anhydrolutein I from (3R,3'R,6'R)-lutein. One published procedure involves treatment of (3R,3'R,6'R)-lutein with a boric acid-naphthalene melt (Zechmeister and Sease, *J. Am. Chem. Soc.*, 65: 1951, 1943). However, under the conditions employed, the total yield of (3R,6'R)-anhydrolutein I based on (3R,3'R,6'R)-lutein was approximately 18%.

Another procedure is based on allylic reduction of (3R, 3'R,6'R)-lutein employing aluminum chloride/lithium aluminum hydride (AlCl₃/LiAlH₄=3/1) (AlHCl₂) complex (Buchecker et al., *Helv. Chim. Acta* 57: 631, 1974). While (3R,6'R)-anhydrolutein I has been obtained from (3R,3'R, 6'R)-lutein in a good yield by this method, due to the sensitivity of the reagents to moisture and air, this process is difficult to scale up for industrial applications.

The most recent partial synthesis of anhydroluteins I, II, and III from (3R,3'R,6'R)-lutein has been reported by Khachik et al. (*J. Chrom. Biomed. Appl.*, 670:219–233, 1995). This method employs 2% concentrated sulfuric acid in acetone to obtain a mixture of anhydroluteins I, II, and III in 92% total yield; among these (3R,6'R)-anhydrolutein I is the major product. While this method can be performed on industrial scale, its scope is limited to the preparation of only anhydroluteins.

SUMMARY OF THE INVENTION

The present invention relates to a process for converting commercially available (3R,3'R,6'R)-lutein to a mixture of (3R,6'R)-α-cryptoxanthin, (3R)-β-cryptoxanthin, and anhydroluteins in one synthetic step in high yields by allylic deoxygenation with a strong acid and a hydride ion donor. The commercially available (3R,3'R,6'R)-lutein contains about 5–7% (3R,3'R)-zeaxanthin which does not react with the reagents employed and can be concentrated in the final product after crystallization.

An alternative process developed according to this invention involves the conversion of (3R,3'R,6'R)-lutein to anhydroluteins I, II, and III with an acid and the subsequent conversion of the latter products to (3R,6'R)-α-cryptoxanthin and (3R)-β-cryptoxanthin with a strong acid and a hydride ion donor.

The mixture of anhydroluteins, (3R,6'R)-α-cryptoxanthin, (3R)-β-cryptoxanthin, and unreacted (3R, 3'R)-zeaxanthin obtained from these reactions can be subjected to batch or column chromatography to obtain individually purified carotenoids.

Yet in another alternative method, the invention relates to a process for converting (3R,3'R,6'R)-lutein directly to (3R, 6'R)-α-cryptoxanthin in nearly quantitative yield by reacting this carotenoid with an alkali metal borohydride such as sodium cyanoborohydride (NaCNBH₃) or sodium (trifluoroacetoxy)borohydride and zinc iodide or bromide in dichloromethane, 1,2-dichloroethane or tert-butyl methyl ether (TBME). Other borohydrides such as borane-trimethylamine or borane-dimethylamine complexes in combination with aluminum chloride in ethers (e.g. ethylene glycol dimethyl ether, tetrahydrofuran) also convert (3R,3'R,6'R)-lutein to (3R,6'R)-α-cryptoxanthin in excellent yields. These borohydride complexes are superior to the toxic sodium cyanoborohydride for reductive deoxygenation of lutein and most importantly the reactions with these reagents can be carried out in non-chlorinated solvents.

This invention also relates to conversion of (3R,3'R,6'R)-lutein to a mixture of anhydrolutein I and (3R,6'R)-α-cryptoxanthin in excellent yield by allylic deoxygenation upon treatment with lithium perchlorate-ether solution in the presence of a hydride ion donor.

According to the present invention, individually purified or nixed carotenoids such as anhydroluteins, (3R,6'R)-α-cryptoxanthin, (3R)-β-cryptoxanthin, and (3R,3'R)-zeaxanthin can be prepared on industrial scale from commercially available (3R,3'R,6'R)-lutein. These carotenoids can be used as nutritional supplements or as food coloring additives. (3R)-β-Cryptoxanthin is also among the vitamin A active carotenoids and can serve as an alternative dietary supplement to retinol. The above carotenoids can be combined with those that are already commercially available to yield a mixture of carotenoids (multicarotenoid) in a ratio that closely resembles the distribution of these compounds in human serum. The resulting multicarotenoid dietary supplement can be used, e.g. in clinical trials, to investigate the efficacy of these compounds in the prevention of cancer, cardiovascular disease, and macular degeneration.

DETAILED DESCRIPTION OF THE INVENTION

According to the present invention, (3R,3'R,6'R)-lutein can undergo allylic deoxygenation to a mixture of (3R,6'R)-α-cryptoxanthin, (3R)-β-cryptoxanthin, and anhydroluteins I, II, III in the presence of a strong acid and a hydride ion donor in a chlorinated solvent (e.g. dichloromethane, 1,2-dichloroethane) at ambient temperature.

Strong acids which may be used in the practice of the invention include acids that have a strong tendency to give up protons (Lowry-Bronsted acids) and acids that readily accept electron pairs (Lewis acids). Examples of Lowry-Bronsted acids which may be used in the practice of the invention include sulfuric acid, hydrochloric acid, trifluoroacetic acid (TFA) and the like. Examples of Lewis acids which may be used in the practice of the invention include boron trifluoride, boron trichloride and titanium tetrachloride.

The hydride ion donors that may be used in the practice of the invention are compounds able to transfer hydride ions. Such compound generally contain one or more electropositive elements of main groups III to VII, particularly main groups III and IV, and one or more hydrides. Examples of hydride donors which may be used in the practice of the invention include aluminum hydride, lithium aluminum hydride, boron hydride, sodium borohydride and organosilanes such as triethylsilane (Et$_3$SiH), trimethylsilane, triphenylsilane and organo-silicon polymers or oligomers having a silicon-hydrogen bond. An example of an organo-silicon polymer is hydrophobic silicon liquid HSL-94 which is commercially available. The most preferred hydride ion donor is Et$_3$SiH. Other trialkylsilanes and arylsilanes can be used but the yields are not as high as those obtained with triethylsilane. Because these hydride ion donors are sensitive to oxygen, the reactions have to be conducted under an inert atmosphere such as nitrogen, argon or helium.

In the presence of a strong acid such as TFA, lutein first undergoes acid-catalyzed dehydration to form anhydroluteins I, II, and III as shown in Scheme 2. Among these, anhydrolutein I is the major product. Protonation of these dehydration products of lutein, results in the formation of a number of resonance hybrid carbocation intermediates. In the presence of a hydride ion donor, these intermediates are converted to (3R,6'R)-α-cryptoxanthin and (3R)-β-cryptoxanthin. As depicted in Scheme 2, the most likely carbocation intermediates which contribute to the formation of the observed products are those formed from protonation of anhydrolutein II and III. Therefore, once lutein is completely converted to its dehydration products, anhydrolutein II and III are gradually converted to (3R,6'R)-α-cryptoxanthin and (3R)-β-cryptoxanthin. This affects the equilibrium between the three dehydration products of lutein and promotes the acid-catalyzed isomerization of anhydrolutein I to anhydroluteins II and III. While a variety of acids readily catalyze dehydration of lutein in a wide range of solvents, the ionic hydrogenation of the resulting anhydroluteins to (3R,6'R)-α-cryptoxanthin and (3R)-β-cryptoxanthin requires a strong acid such as TFA in a chlorinated solvent, preferably, dichloromethane. This, to some extent, results in E/Z (trans/cis)-isomerization of the polyene chain of the carotenoids involved. Therefore the above all-E(trans)-carotenoids in the final products are accompanied by approximately 15–25% of their Z(cis)-isomers.

Depending on the molar equivalence of strong acid (e.g., TFA) relative to (3R,3'R,6'R)-lutein and the volume of the solvent employed, the yield and relative composition of the individual carotenoids in the final product may vary. While the dehydration step of these transformations with TFA is nearly quantitative, the resulting anhydroluteins are not completely converted to α- and β-cryptoxanthin in the ionic hydrogenation step. Therefore depending on the reaction conditions, approximately 18–34% of anhydroluteins may remain unchanged in the final products.

The crude products from the reaction of (3R,3'R,6'R)-lutein with TFA/Et$_3$SiH can be directly subjected to batch or column chromatography employing a combination of a hydrocarbon solvent (pentane, hexane, heptane, cyclohexane, petroleum ether) and acetone or methyl ethyl ketone. The ratio of the hydrocarbon to acetone or methyl ethyl ketone may vary from 9/1 to 4/1. Instead of acetone or methyl ethyl ketone other solvents such as ethyl acetate, tetrahydrofuran or C$_4$–C$_6$-ethers may also be employed with the same results. Examples of C$_4$–C$_6$-ethers are; diethyl ether, diisopropyl ether, t-butyl methyl ether, 1,2-dimethoxyethane, and tetrahydrofuran. The chromatography adsorbent (stationary phase) is preferably n-silica gel. In a typical separation, a crude mixture of anhydroluteins, (3R,6'R)-α-cryptoxanthin, (3R)-β-cryptoxanthin, and unreacted (3R,3'R)-zeaxanthin is subjected to batch or column chromatography to obtain three major fractions. The first fraction consists of a mixture of (3R,6'R)-α-cryptoxanthin and (3R)-β-cryptoxanthin, the second fraction is a mixture of anhydroluteins, and the third fraction is the unreacted (3R, 3'R)-zeaxanthin.

SCHEME 2.

Proposed pathways for transformation of (3R,3'R,6'R)-lutein into a mixture of anhydroluteins I, II, III, (3R,6'R)-α-cryptoxanthin, and (3R)-β-cryptoxanthin by ionic hydrogenation.

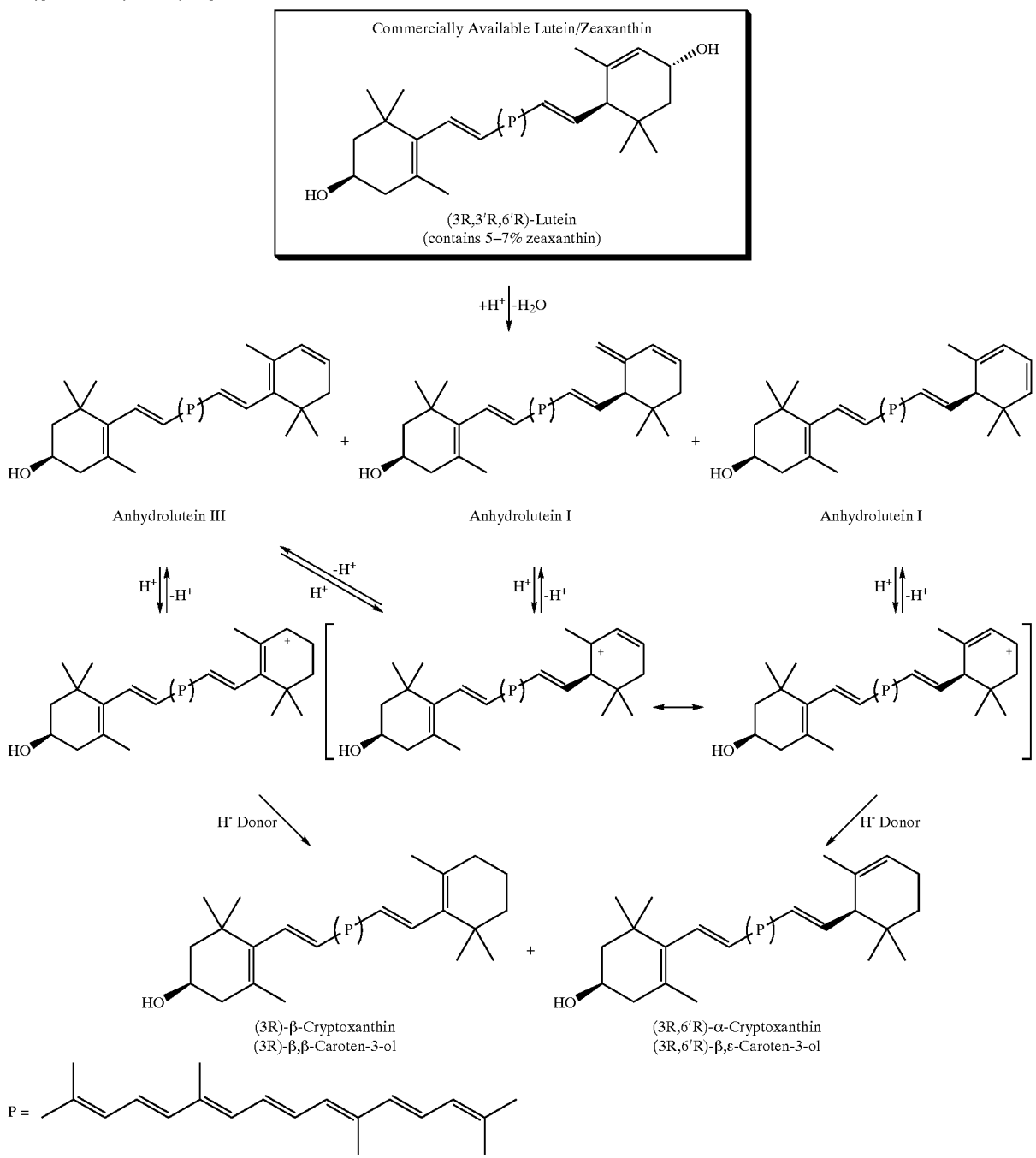

The present invention further relates an alternative route to these carotenoids by first converting (3R,3'R,6'R)-lutein to anhydroluteins I, II, and III in acidic solutions, isolating the products, and then reacting these dehydration products with a strong acid (e.g., TFA in the presence of a hydride ion donor e.g., an organosilane such as Et$_3$SiH) to obtain a mixture of (3R,6'R)-α-cryptoxanthin (all-E+Z) and (3R)-β-cryptoxanthin (all-E+Z) as well as some unreacted anhydroluteins (all-E+Z).

While ionic hydrogenation of cyclic and acyclic olefins with strong acids e.g., (TFA) and hydride ion donors (e.g., Et$_3$SiH) has been known for several decades, the application of this reaction to the industrial production of carotenoids has not been reported. This invention applies the concept of ionic hydrogenation of cyclic alcohols to commercially available (3R,3'R,6'R)-lutein employing strong acids and hydride ion donors to convert this carotenoid to a mixture of (3R,6'R)-α-cryptoxanthin, (3R)-β-cryptoxanthin, and anhydroluteins. This is a simple one-step reaction and can be conducted at room temperature and under mild reaction conditions.

This invention further demonstrates that (3R,3′R,6′R)-lutein can be converted directly to (3R,6′R)-α-cryptoxanthin by reaction with sodium cyanoborohydride and zinc iodide or zinc bromide in dichloromethane or 1,2-dichloroethane or ether solvent such as tert-butyl methyl ether (TBME) in yields of up to 90%. This reagent has been reported to effect the reductive deoxygenation of aryl aldehydes and ketones as well as benzylic, allylic, and tertiary alcohols (C. K. Lau, *J. Org. Chem,* 51:3038–43, 1986). Another literature example of the use of this reagent is the deoxygenation of furanmethanols (Jeronimo da S. Costa et al., *J. Braz. Chem Soc.,* 5:113–116, 1994). However, the application of this reagent for reductive deoxygenation of carotenoids has not been reported. The proposed mechanism for this reduction is shown in Scheme 3.

SCHEME 3.

Proposed mechanism for the conversion of (3R,3′R,6′R)-lutein to (3R,6′R)-α-cryptoxanthin by an alkali metal borohydride and zinc halide.

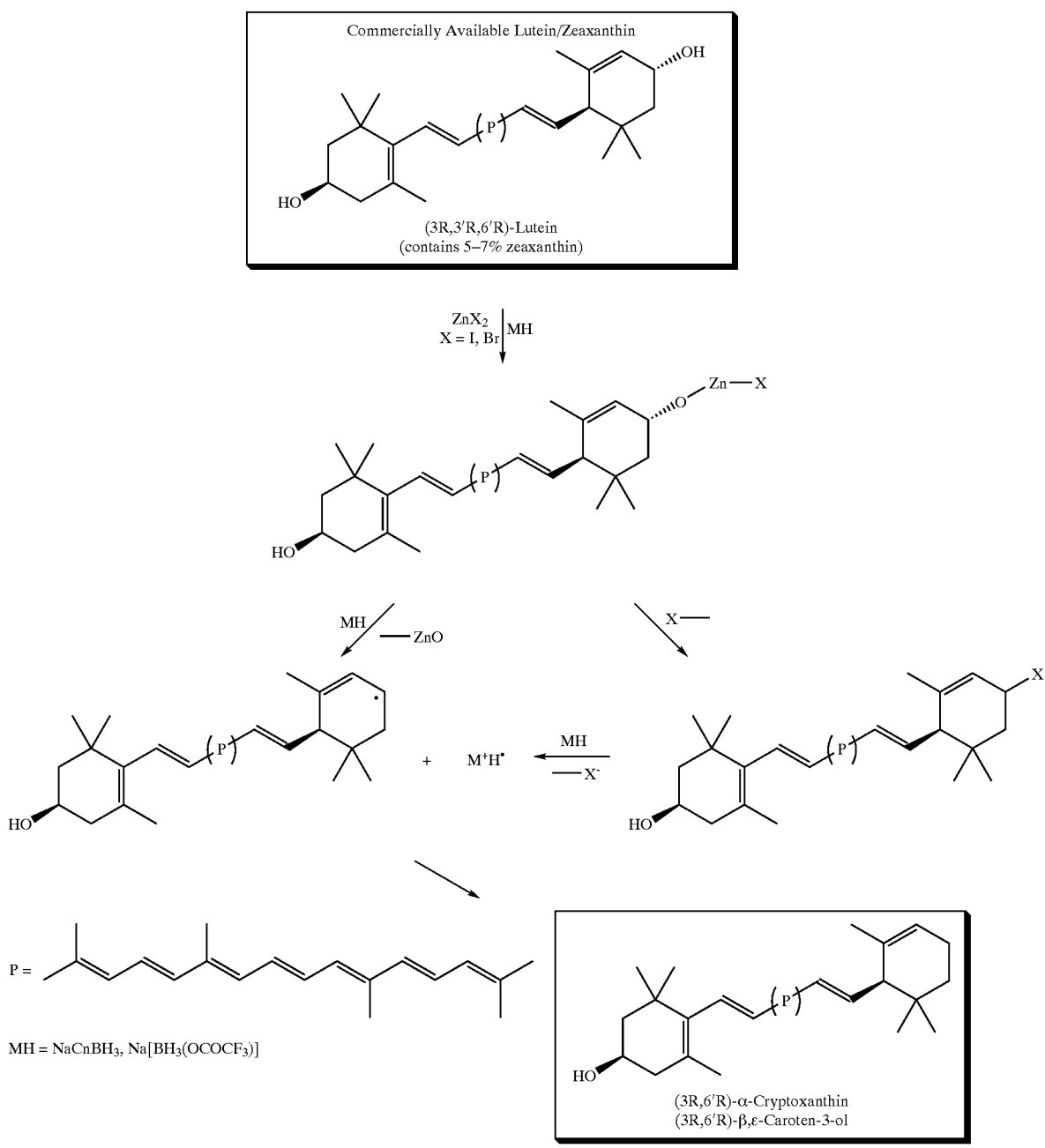

Instead of sodium cyanoborohydride, sodium (trifluoroacetoxy)borohydride (generated from sodium borohydride and trifluoroacetic acid) may be used with zinc bromide or zinc iodide. In this reaction, zinc bromide is preferred since it gives (3R,6'R)-α-cryptoxanthin nearly quantitatively as the sole product while zinc iodide results in the formation of anhydroluteins as side products. It is interesting to note that lithium (trifluoroacetoxy) borohydride (generated from lithium borohydride and trifluoroacetic acid) in the presence of zinc iodide or zinc bromide does not react with lutein. The best solvents for this reaction are chlorinated solvents such as dichloromethane or 1,2-dichloroethane. The reaction of sodium borohydride and zinc iodide with lutein results in the formation of a mixture of (3R,6'R)-α-cryptoxanthin, anhydrolutein, and considerable amount of lutein remains unreacted. When zinc iodide is replaced with zinc bromide, the reaction does not proceed. The combinations of lithium borohydride with either zinc iodide or zinc bromide are also found to be unreactive for allylic deoxygenation of lutein.

To avoid the use of toxic sodium cyanoborohydride and chlorinated solvents, the invention further demonstrates that (3R,3'R,6'R)-lutein can be transformed into (3R,6'R)-α-cryptoxanthin in yields of up to 90% employing borane-trimethyamine ($Me_3N.BH_3$) or borane-dimethylamine ($Me_2NH.BH_3$) complexes as the reducing agents in combination with aluminum chloride ($AlCl_3$) in ethers, preferably tetrahydrofuran or 1,2-dimethoxyethane (ethylene glycol dimethyl ether). These borohydride complexes in combination with aluminum chloride are much more reactive than sodium cyanoborohydride/zinc halide and the reaction is normally completed within one to two hours at ambient temperature and under an inert atmosphere (e.g. nitrogen or argon). Because of the excellent solubility of lutein and borane-amine complexes in THF and 1,2-dimethoxyethane, the reductive deoxygenation in these solvents are completed within one to two hours. When borane-trimethyamine or borane-dimethylamine complexes are employed in combination with zinc iodide or zinc bromide, lutein does not undergo reductive deoxygenation. There are no literature reports on the reductive deoxygenation of carotenoids with borane-trimethyamine or borane-dimethylamine complexes in combination with aluminum chloride.

Similarly, this invention further demonstrates another alternative method for deoxygenation of lutein by employing lithium perchlorate-ether (e.g., 3.0 M in diethyl ether) solution and a hydride ion (e.g., triethylsilane) as reagents. In this reaction, (3R,3'R,6'R)-lutein undergoes selective deoxygenation to give a mixture of mostly anhydrolutein I and (3R,6'R)-α-cryptoxanthin and no (3R)-β-cryptoxanthin is obtained. The selective deoxygenation of allylic alcohols and acetates by lithium perchlorate ($LiClO_4$) promoted triethylsilane reduction has been reported for a number of cyclic allylic alcohols and acetates (Wustrow et al., *Tetrahedron Lett.*, 35:61–64, 1994). However, there are no reports on the application of this reagent for production of α-cryptoxanthin from lutein. According to literature reports, this reagent is thought to induce the ionization of the allylic oxygen bond activating it toward nucleophilic substitution. Therefore in this reaction a hydride generated from triethylsilane could act as a nucleophile to promote the reductive deoxygenation of lutein to α-cryptoxanthin. The formation of anhydrolutein I as the side product of this reaction is in agreement with the involvement of a carbocation intermediate.

The commercially available (3R,3'R,6'R)-lutein employed in these reactions may be isolated from extracts of marigold flowers: and may contain approximately 5–7% (3R,3'R)-zeaxanthin. Because (3R,3'R)-zeaxanthin does not react with TFA/organosilanes or alkali metal borohydride/zinc halide or $Me_3N.BH_3/AlCl_3$ or $Me_2NH.BH_3/AlCl_3$ or $LiClO_4$/organosilanes, this carotenoid can be fully recovered and its concentration in the final product can be increased by crystallization. Optionally, pure (3R,3'R)-zeaxanthin may be recovered from the crude products of various reactions by column chromatography.

Reagents and Starting Materials

Two types of (3R,3'R,6'R)-lutein may be employed as starting materials in this invention, these are: 1) commercially available (3R,3'R,6'R)-lutein with approximately 85% total carotenoid purity and 2) crystalline lutein with greater than 97% total carotenoid purity according to the process described in WO99/20587. Both starting materials are prepared from crude saponified extracts of Marigold flowers and contain approximately 5–7% (3R,3'R)-zeaxanthin. Mixtures of these two starting materials may also be employed.

The crude saponified extract of Marigold flower containing (3R,3'R,6'R)-lutein and several minor carotenoids may be prepared according to the process described in WO99/20587, (3R,3'R,6'R)-Lutein (97% total carotenoid purity) containing approximately 5–7% zeaxanthin may also be purified from this extract according to this procedure. Commercially available (3R,3'R,6'R)-lutein (85% total carotenoid) may be obtained from Kemin Industries (Des Moines, Iowa). All reagents used in this invention are commercially available (Aldrich Chemical Co., Milwaukee, Wis.) and are used without further purification. The carotenoid composition of the 85% and 97% lutein is shown in Table 1. The reactions conducted with the commercially available (3R,3'R,6'R)-lutein (85% purity) proved to be much more challenging than the 95% pure compound with regard to the optimization of yield and the amount of the reagents needed to complete the reactions. Therefore, only the reactions of 85% lutein are described here in great detail.

TABLE 1

Carotenoid composition of 85% and 97% (3R,3'R,6'R)-lutein isolated from marigold flowers.

| Marigold Carotenoids | Composition | |
|---|---|---|
| | 85% total carotenoid purity | 97% total carotenoid purity |
| (all-E,3R,3'R,6'R)-lutein[a] | 91.0 | 95.0 |
| (all-E,3R,3'R)-zeaxanthin | 6.54 | 5.0 |
| Anhydroluteins (lutein dehydration products) | 0.43 | 0.0 |
| β-carotene | 0.35 | 0.0 |
| α-cryptoxanthin | 0.41 | 0.0 |
| β-cryptoxanthin | 0.38 | 0.0 |
| 3-hydroxy-β,ε-caroten-3'-one | 0.89 | 0.0 |
| Total | 100.0 | 100.0 |

[a]The 85% and 97% lutein did not contain any significant amount of Z (cis)-luteins.

High Performance Liquid Chromatographic (HPLC) conditions for monitoring the course of the reactions. All separations were conducted on a Hewlett-Packard (HP) 1050 High Performance Liquid Chromatography (HPLC) system equipped with a rapid-scanning UV/visible photodiode array detector, and an HP-1050 autosampler. The data were stored and processed by means of Compaq DeskPro 590 computing system using the HP Chem-Station program (version A.05.02) on Windows-97, in combination with a high resolution color display monitor. Model MaxTech MPR11, and an HP-Laserjet4 Plus printer. The absorption spectra of the carotenoids were recorded between 200 and 600 nm at a rate of 12 spectra/min.

Reversed phase separations were carried out on a Microsorb (25-cm length×4.6 mm i.d.) $C_{18}$ (5-μm spherical particles) column (Rainin Instrument Co., Woburn, Mass.), which was protected with a Brownlee guard cartridge (3-cm length×4.6 mm i.d.) packed with spheri-5-$C_{18}$ (5-μm particle size). A combination of isocratic and gradient HPLC employing a two pump solvent module was used with this eluent. Pump A pumped a mixture of acetonitrile/methanol (9/1, v:v) and pump B pumped a mixture of hexane/dichloromethane/methanol/DIPEA (N,N-diisopropylethylamine) (4.5/4.5/0.99/0.01, v:v:v:v). At time-zero, an isocratic mixture of acetonitrile (85.5%), methanol (9.995%), dichloromethane (2.25%), hexane (2.25%), and DIPEA (0.005%) (95% pump A, 5% pump B) was pumped for 10 min. After 10 min, a linear gradient was run for 30 min resulting in a final composition of acetonitrile (40.5%), methanol (9.95%), dichloromethane (24.75%), hexane (24.75%), DIPEA (0.0551%) (45% pump A, 55% plump B). The column flow rate was 0.70 mL/min. The HPLC injection solvent consisted of a mixture of acetonitrite (85%), dichloromethane (2.5%), hexane (2.5%), and methanol (10%). HPLC runs were completed in 30 min. At the end of each run, the column was equilibrated under the initial isocratic conditions for 20 min. HPLC runs were monitored at 446 nm. The HPLC retention times and the absorption maxima of carotenoids which were monitored in the course of various dehydration and ionic hydrogenation reactions of (3R,3'R,6'R)-lutein with trifluoroacetic acid (TFA) in the presence of a hydride ion donor are shown in Table 2.

TABLE 2

HPLC retention times and the UV-Visible absorption maxima of carotenoids monitored in the course of dehydration and ionic hydrogenation of (3R,3'R,6'R)-lutein.

| Entry | Carotenoids[1] | HPLC Retention Time (Min) | UV-Visible[2,3] Absorption Maxima (nm) |
|---|---|---|---|
| 1 | (3R,3'R,6'R)-Lutein | 9.56 | (424), 446, 476 |
| 2 | (all-E, 3R,3'R)-Zeaxanthin | 10.22 | (428), 454, 482 |
| 3 | (9Z, 3R,3'R)-Zeaxanthin | 12.19 | 340, (424), 450, 474 |
| 4 | (13Z, 3R,3'R)-Zeaxanthin | 12.77 | 340, (420), 446, 472 |
| 5 | (all-E, 3R,6'R)-Aphydrolntein I | 19.26 | (424), 448, 476 |
| 6 | (Z, 3R,6'R)-Anhydrolutein I | 19.78 | 332, (420), 440, 468 |
| 7 | (all-E, 3R,6'R)-2',3'-Anhydrolutein II | 20.37 | (424), 446, 476 |
| 8 | (Z, 3R,6'R)-2',3'-Anhyclrolutein II | 20.77 | 334, (418), 440, 468 |
| 9 | (all-E, 3R)-3',4'-Anhydrolutein III | 21.27 | 466 |
| 10 | (Z, 3R)-3',4'-Anhydrolutein III | 21.75 | 356, 456 |
| 11 | (3R,6'R)-a-Cryptoxanthin (all-E + Z) | 23.37 | (424), 446, 476 |
| 12 | (all-E, 3R)-β-Cryptoxanthin | 24.10 | (428), 452, 480 |
| 13 | (Z, 3R)-β-Cryptoxanthin | 24.66 | 340, (424), 450, 474 |

[1]location of the Z(cis)-bond in anhydroluteins I, II, III, α-cryptoxanthin, and β-cryptoxanthin is not known.
[2]UV-visible spectra were obtained by a photodiode array detector in the HPLC solvents.
[3]Values in parentheses indicate points of inflection.

Reactions of (3R,3'R,6'R)-lutein with TFA/Et$_3$SiH. In a typical experiment, triethylsilane (0.94 mmol) (2.1 molar equivalence of lutein) is added to a solution of 85% commercially available (3R,3'R,6'R)-lutein (0.300 g of 85%, 0.255 g, 0.448 mmol) in 25 ml of a chlorinated solvent (dichloromethane or 1,2-dichloroethane) kept under an inert atmosphere (i.e. nitrogen or argon). Trifluoroacetic acid (TFA, 0.12 ml, 0.178 g, 1.56 mmol) (3.5 molar equivalence of lutein) is then added all at once at ambient temperature. No heat is generated as a result of this rapid addition. Alternatively, TFA may be added in a small volume (5 ml) of the solvent within a few minutes with the same results. The reaction mixture immediately turns dark red. The mixture is stirred at room temperature and the course of the reaction is followed by HPLC. Depending on the concentration of TFA, the nature of the solvent, and the purity of triethylsilane, the reaction time vary from 6 to 8 hours. HPLC studies of the course of the reaction have revealed that under these conditions lutein is quantitatively dehydrated to form anhydroluteins I, II, III within the first two hours. The resulting carotenoids then slowly undergo ionic hydrogenation to form α-cryptoxanthin and β-cryptoxanthin. The rate of the ionic hydrogenation step is greatly dependent on the concentration of TFA and the purity of triethylsilane. Triethylsilane is sensitive to air and despite the fact that it is stored under an inert atmosphere (nitrogen or argon), it gradually looses its potency during long-term storage. Therefore, freshly distilled or commercially available triethylsilane packed and stored under nitrogen should be used. The concentration of TEA in a given volume of the solvent also plays an important role in the outcome of the reaction. At higher concentrations of TEA than stated above, the reaction is faster and results in a complete conversion of lutein to α-cryptoxanthin and β-cryptoxanthin but considerable amount of degradation and (E/Z)-isomerization of carotenoids is observed. At the end of the reaction, approximately 18–34% of the anhydroluteins may remain unreacted. The work-up consists of treating the crude product with 5% sodium bicarbonate or potassium bicarbonate to neutralize the TFA. This is followed by gradual displacement of the chlorinated solvent (dichloromethane (b.p=40° C.) or 1,2-dichloroethane (b.p=83° C.)) with a higher boiling alcohol, preferably 2-propanol (b.p=82.4° C.), by distillation under atmospheric pressure. Once the chlorinated solvent is removed, most of the alcohol is distilled under reduced pressure until carotenoids crystallize from aqueous alcohol. The crystals are removed on a centrifuge or by filtration and the solid product is washed with a small volume of acetone (10 ml) to remove the water. After filtration, the solid is dried under high vacuum at 60° C. to give 223 mg of a mixture of (3R,6'R)-α-cryptoxanthin (all-E+Z), (3R)-p-cryptoxanthin (all-E+Z), and anhydroluteins (all-E+Z) as well as the recovered (3R,3'R)-zeaxanthin (all-E+9Z+13Z). Based on the purity and the weight of the starting lutein, the total yield of carotenoids in the mixture is in the range of 80–90%. While (3R,3'R,6'R)-lutein is completely consumed during this reaction, (3R,3'R)-zeaxanthin does not react with TFA/Et$_3$SiH and is fully recovered in the final products. The total weight (mg) and the relative distribution of carotenoids in the final products of the reaction of (3R,3'R,6'R)-lutein with TFA/Et$_3$SiH in chlorinated solvents were determined by HPLC and are shown in Table 3.

TABLE 3

The relative distribution of citrotenoids in the products of the reaction of commercial (3R, 3'R, 6'R)-lutein (85% pure) with trifluoroacetic acid (TFA) and triethylsilane (Et₃SiH) in chlorinated solvents.*

| Lutein, 0.300 g (85%) ≈ 0.255 g, 0.448 mmol | Et₃SiH (mmol) | TFA (mmol) Reaction Time (h) | Zeaxanthin (All-E + 9Z + 13Z) (recovered) (%) | Anhydro-luteins (All-E + Z) (%) | α-Crypto-xanthin (All-E + Z) (%) | β-Crypto-xanthin (All-E + Z) (%) | Total Weight (g) & % yield of Carotenoids |
|---|---|---|---|---|---|---|---|
| Solvent | | | | | | | |
| Dichloro-methane | 0.94 | 1.56  8 h | 17.0 | 18.7 | 25.2 | 39.1 | 223 (90%) |
| Dichloro-methane | 0.94 | 1.56  6 h | 9.0 | 34.1 | 29.7 | 27.2 | 218 (88%) |
| Dichloro-methane | 0.94 | 1.36  10 h | 9.1 | 32.8 | 26.4 | 31.7 | 198 (80%) |
| Dichloro-methane | 0.94 | 1.36  5 H | 10.2 | 52.9 | 16.0 | 20.9 | 221 (89%) |
| 1,2-Dichloro-ethane | 0.94 | 1.56  8 h | 14.2 | 30.8 | 28.2 | 26.8 | 216 (87%) |

*In all experiments, TFA was added to a solution of (3R, 3'R, 6'R)-lutein and triethylsilane in 25 ml of the chlorinated solvent under an atmosphere of nitrogen at ambient temperature and the course of the reaction was followed by HPLC.

Finally, the product can be washed with a hydrocarbon solvent (e.g., pentane, hexane, heptane, petroleum ether) at 0° C. or lower temperatures (0° C. to −20° C.) to dissolve and separate the Z(cis)-isomers of carotenoids from their corresponding all-E(trans)-carotenoids. The solids from this hydrocarbon wash consist mainly of all-E(trans)-isomers of carotenoids and is particularly enriched in zeaxanthin. The relative distribution of carotenoids in a typical crude product from ionic hydrogenation of lutein with TFA/Et₃SiH and the separation of the all-E(trans)-carotenoids from their corresponding Z(cis)-isomers by treatment with hexane at 0° C. is shown in Table 4.

needed to complete the reaction. This is presumably due to the presence of impurities (mostly fatty acids) in the 85% pure lutein. In addition, triethylsilane is air sensitive and despite the fact that it is stored under an inert atmosphere (nitrogen), it gradually looses its potency during long-term storage.

The molar equivalence of TFA relative to (3R,3'R,6'R)-lutein can affect the ratio of c-cryptoxanthin and β-cryptoxanthin. For example, if the molar equivalence of TFA to lutein is increased from 3.5 to 5, higher yields of α-cryptoxanthin relative to β-cryptoxanthin is obtained and the reactions are normally completed within several hours.

TABLE 4

The relative distribution of all-E(trans)-carotenoids and their geometrical Z(cis)-isomers in a typical crude produce from the reaction of lutein with TFA/Et₃SiH and the distribution of the isomers in hexane soluble and insoluble fractions.

| Carotenoids | Relative Distribution (%)[a] | | |
|---|---|---|---|
| | Crude Product | Hexane Soluble | Hexane Insoluble Solids |
| all-E(trans)-Zeaxanthin  9Z(cis)  13Z(cis) | 10.5  3.0  3.5 | 0.9  0.6  0.5 | 33.5  4.3  5.8 |
| Total | 17.0 | 2.0 | 43.6 |
| all-E(trans)-Anhydrolutein I  Z(cis) | 7.4  5.3  12.7 | 3.4  2.4  5.8 | 3.4  1.3  4.7 |
| Total | | | |
| all-E(trans)-Anhydrolutein II  Z(cis) | 1.5  2.4 | 4.0  2.2 | 3.9  1.0 |
| Total | 3.9 | 6.2 | 4.9 |
| all-E(trans)-Anhydrolutein III  Z(cis) | 1.1  1.0 | 1.1  1.3 | 1.1  0.7 |
| Total | 2.1 | 2.4 | 1.8 |
| α-cryptoxanthin (all-E + Z)[b] | 25.2 | 32.0 | 18.5 |
| β-cryptoxanthin (all-E + Z)[b] | 39.1 | 51.6 | 26.5 |

[a] Carotenoids were separated by HPLC.
[b] The HPLC peaks of the all-E(trans)-isomers were not well-resolved from their Z(cis)-isomers.

In all experiments listed in Table 3, much higher molar equivalence of triethylsilane relative to lutein (2.1:1) was However, under these conditions, degradation of carotenoids results in a poor yield. While high concentrations of TFA in dichloromethane also result in complete conversion of the intermediate anhydroluteins to α-cryptoxanthin and β-cryptoxanthin, the overall yield of carotenoids is greatly compromised. Longer reaction times than 6–8 h results in isomerization of α-cryptoxanthin and β-cryptoxanthin and is also accompanied by the loss of carotenoids.

The choice of the chlorinated solvents in the reaction of lutein with TFA/Et₃SiH is also limited since only dichloromethane and 1,2-dichloroethane were found to be effective in this reaction. Chloroform only afforded the dehydration products of lutein. Similarly, other non-chlorinated solvents such as alcohols, hydrocarbons, and ethers only afforded anhydroluteins and did not promote the ionic hydrogenation of these carotenoids to α-cryptoxanthin and β-cryptoxanthin. Reaction of lutein with TFA/Et₃SiH in toluene also afforded the desired products but in contrast to the reaction in dichloromethane, much higher molar equivalence of TFA to lutein was needed. Under these conditions most of the carotenoids were destroyed resulting in a low yield of α-cryptoxanthin and β-cryptoxanthin.

The individual carotenoids from the reactions described above, were isolated and purified from the crude mixture of products by flash column chromatography followed by preparative HPLC and their identity was established by UV-Visible spectrophotometry, mass spectrometry, and ¹H-nuclear magnetic resonance (¹H-NMR) spectroscopy.

Optionally, the crude product from the reaction of lutein with TFA/Et₃SiH may be purified by column chromatography to separate and purify carotenoids of interest. In a typical experiment, 0.3 g of a crude mixture of products consisting of (3R,6'R)-α-cryptoxanthin (all-E+Z), (3R)-β-cryptoxanthin (all-E+Z), anhydroluteins (all-E+Z) and (3R, 3'R)-zeaxanthin (all-E+9Z+13Z) is purified on a flash column (20 cm 1×3.5 cm i.d.) packed with n-silica gel (50 g) employing a mixture of hexane/acetone (9/1) as eluent. In the order of elution, three major fractions are collected comprising: 1) a pure mixture of (3R,6'R)-α-cryptoxanthin (all-E+Z) and (3R)-β-cryptoxanthin (all-E+Z), 2) a pure mixture of anhydroluteins, and 3) unreacted zeaxanthin. Other hydrocarbon solvents such as cyclohexane, heptane, pentane, petroleum ether can also be employed with acetone. The ratio of the hydrocarbon solvent to acetone may vary from 9/1 to 4/1. Instead of acetone, other solvents such as methyl ethyl ketone, ethyl acetate, tetrahydrofuran or $C_4$–$C_6$-ethers may also be used.

Triethylsilanol (b.p.=158° C./760 mmHg) and hexaethyldisiloxane (b.p.=233–236° C./760 mmHg) are generally produced as byproducts of the ionic hydrogenation during work-up. These relatively high boiling byproducts can be removed from the final product during crystallization.

In particular the invention relates to a method of converting a mixture of (3R,3'R,6'R)-lutein containing (3R,3'R)-zeaxanthin to a mixture of (3R,6'R)-α-cryptoxanthin, (3R)-β-cryptoxanthin, and anhydroluteins comprising:

a) dissolving the mixture of (3R,3'R,6'R)-lutein and (3R, 3'R)-zeaxanthin in an appropriate volume of a chlorinated solvent and adding a hydride ion donor under an inert atmosphere to obtain a mixture;

b) adding a strong acid to the mixture at ambient temperature and under conditions that promote the ionic hydrogenation reaction to obtain a crude product;

c) neutralizing the acid in the crude product by a addition of a base;

d) removing the chlorinated solvent thereby obtaining crystallized carotenoids;

e) collecting the crystals; and f) drying the final product; and g) optionally subjecting the crude product to column chromatography to obtain the individually purified carotenoids.

Preferably, the mixture is the 85% commercially available or highly purified (3R,3'R,6'R)-lutein containing about 5–7% (3R,3'R)-zeaxanthin. Preferably, the chlorinated solvent is dichloromethane or 1,2-dichloroethane. Also preferably, the hydride ion donor is triethyl silane and the strong acid is TFA, preferably at 2.1 molar equivalent of triethylsilane to lutein. Also preferably, 1 equivalent of acid is added to 3.5 molar equivalent of lutein. Most preferably, one mole equivalent of (3R,3'R,6'R)-lutein, containing about 5–7% (3R,3'R)-zeaxanthin in a chlorinated solvent is stirred with about 2–3 equivalent of Et₃SiH and about 3.0–3.5 equivalent of TFA at ambient temperature for about 5–10 hours under an inert atmosphere.

Preferably, the base is sodium or potassium hydrogen carbonate or an organic base such as triethylamine.

Preferably, the chlorinated solvents are removed by distilling off the chlorinated solvent under reduced pressure and removing it with the gradual displacement with a higher boiling alcohol, preferably 2-propanol; and the alcohol is evaporated under reduced pressure until carotenoids then crystallize from aqueous alcohol.

Preferably, the crystals are collected by filtration or on a centrifuge and the crystals are washed with a small volume of acetone or alcohol.

The final product may be dried under vacuum, preferably at about 40–60° C. under high vacuum to obtain a mixture of carotenoids.

The invention further relates to a process for separating the Z(cis)-isomers of carotenoids from their all-E(trans)-compounds by washing the crystalline product with a $C_5$–$C_7$ hydrocarbon or petroleum ether at 0° C. or lower (0° C. to –20° C.) to remove the Z-isomers and obtain a crystalline product comprising of predominantly all-E isomers of (3R, 6'R)-α-cryptoxanthin, (3R)-β-cryptoxanthin, anhydroluteins as well as a high concentration of the unreacted zeaxanthin. Examples of $C_5$–$C_7$ hydrocarbons include pentane, cyclopentane, hexane, cyclohexane, heptane, benzene and toluene.

The invention further relates to a process for separation and purification of the individual carotenoids by column chromatography on n-silica gel employing $C_5$–$C_7$ hydrocarbon or petroleum ether in combination with acetone or methyl ethyl ketone or ethyl acetate or THF or $C_4$–$C_6$-ethers.

Acid-catalyzed dehydration of (3R,3'R,6'R)-lutein. As mentioned above, an alternative approach to this invention is to quantitatively convert (3R,3'R,6'R)-lutein to a mixture of anhydroluteins I, II, and III and then react these carotenoids in a subsequent step with Et₃SiH/TFA to obtain a mixture of (3R,6'R)-α-cryptoxanthin and (3R)-β-cryptoxanthin.

In a typical experiment, the commercially available (85% total carotenoids) or highly purified (3R,3'R,6'R)-lutein (97% total carotenoids) containing about 5–7% (3R,3'R)-zeaxanthin is dehydrated to yield a mixture of (3R,6'R)-anhydrolutein I, (3R,6'R)-2',3'-anhydrolutein II, and (3R)-3',4'-anhydrolutein III and their geometrical isomers in the presence of TFA or an aqueous acid such as sulfuric acid, hydrochloric acid, or phosphoric acid and the like in a variety of solvents. The relative composition of anhydroluteins in the crude products from various dehydration reactions has been determined by HPLC and the results are shown in Table 5.

Also preferably, the product is dried at 60° C. under high vacuum to obtain a mixture of anhydroluteins.

Reaction of anhydroluteins I, II, and III with $Et_3SiH/TFA$. The reaction of a mixture of anhydroluteins I, II, and III with $Et_3SiH/TFA$ in a chlorinated solvent (e.g. dichloromethane, 1,2-dichloroethane) or toluene at ambient temperature under an atmosphere of nitrogen affords a mixture of (3R,6'R)-α-cryptoxanthin and (3R)-β-cryptoxanthin (all-E+Z) as well as some unreacted anhydroluteins (all-E+Z). (3R,3'R)-Zeaxanthin which is present in minute quantities in the

TABLE 5

The products of acid-catalyzed dehydration of (3R, 3'R, 6'R)-lutein.*

| Lutein (85%), g Containing 5–7% Zeaxanthin (Reaction Time, h) | Acid (ml) Solvent (ml) | Recovered Zeaxanthin (all-E + 9Z + 13Z) (%) | Anhydrointeins (all-E + Z) (%) | | |
|---|---|---|---|---|---|
| | | | I | II | III |
| 0.283 (24 h) | $H_2SO_4$ (50%), 0.4 ml THF, 10 ml | 6.4 | 57.6 | 10.0 | 26.0 |
| 0.283 (2 h) | $H_2SO_4$ (50%), 0.8 ml THF, 10 ml | 7.9 | 61.5 | 8.6 | 22.0 |
| 3.36 (2 h) | $H_2SO_4$ (50%), 10 ml THF, 150 ml | 6.9 | 58.0 | 8.8 | 26.3 |
| 0.283 (3 h) | $H_2SO_4$ in EtOH (50%), 0.8 ml THF, 10 ml | 6.8 | 62.3 | 9.8 | 21.1 |
| 0.283 (3 h) | $CF_3CO_2H$, 0.05 ml $CH_2Cl_2$, 25 ml | 9.7 | 71.0 | 8.2 | 11.1 |
| 1.00 (21 h) | $CF_3CO_2H$, 0.20 ml $CHCl_3$, 150 ml | 10.8 | 74.9 | 9.0 | 5.3 |
| 0.283 (5 h) | $CF_3CO_2H$, 0.10 ml Toluene, 10 ml | 9.9 | 59.7 | 13.8 | 16.6 |
| 0.283 (1 h) | $BF_3 \cdot Et_2O$, 0.64 ml THF, 10 ml | 7.6 | 85.3 | 4.2 | 2.9 |

*All experiments were conducted at ambient temperature under an atmosphere of nitrogen.

Therefore the invention further relates to a method for converting the commercially available (85% total carotenoids) or highly purified (3R,3'R,6'R)-lutein (97% total carotenoids) containing approximately 5–7% (3R,3'R)-zeaxanthin to a mixture of (3R,6'R)-anhydrolutein I, (3R,6'R)-2',3'-anhydrolutein II, and (3R)-3',4'-anhydrolutein III and their mono-Z geometrical isomers in the presence of TFA or an aqueous acid such as sulfuric acid, hydrochloric acid, or phosphoric acid and the like in a variety of solvents including without limitation tetrahydrofuran (THF), toluene, acetone, $C_1$–$C_4$ alcohols, $C_4$–$C_6$ ethers, and chlorinated solvents to obtain a crude product; and a) neutralizing the acid in the crude product;
b) removing the solvent;
c) collecting the crystals;
d) drying the final product; and
e) using the dried product directly to convert these carotenoids to α-cryptoxanthin and β-cryptoxanthin.

Examples of $C_1$–$C_4$ alcohols include methanol, ethanol, propanol, 2-propanol, and butanol. Examples of $C_4$–$C_6$ ethers include diethyl ether, diisopropyl ether, tetrahydrofuran, t-butyl methyl ether, and 1,2-dimethoxyethane (ethylene glycol dimethyl ether).

Preferably, the acid is neutralized by addition of a solution of sodium or potassium hydroxide or an organic base.

Also preferably, the solvent is removed by the gradual displacement with a higher boiling $C_5$–$C_7$ hydrocarbon solvent or an alcohol; and the solvent is removed under reduced pressure until anhydroluteins crystallize.

Also preferably, the crystals are collected by filtration or on a centrifuge and the crystals are washed with a small volume of the solvent or acetone.

starting material does not react with the reagent and can be recovered. The reactions are normally completed within about 2.5–6 hours.

In a preferred embodiment, one mole equivalent of anhydroluteins I, II, and III, containing 6–10% (3R,3'R)-zeaxanthin in a chlorinated solvent or toluene is stirred with about 2.8–3 equivalent of $Et_3SiH$ and about 3.8–12 equivalent of TFA at ambient temperature for about 2.5–6 hours under an inert atmosphere to give a mixture of unreacted anhydroluteins, (3R,6'R)-α-cryptoxanthin, (3R)-β-cryptoxanthin and recovered (3R,3'R)-zeaxanthin. The product mixture may be worked up by neutralizing the acid with an aqueous or an organic base and displacing the chlorinated solvent or toluene with a higher boiling alcohol by distillation under reduced pressure until carotenoids crystallize from the aqueous alcohol. The crystalline carotenoids may then be washed with acetone or alcohol, and dried under high vacuum at about 40–60° C.

The composition of carotenoids in the crude products from typical experiments in dichloromethane and toluene are shown in Table 6.

The reaction in dichloromethane gives a relatively good yield of products as opposed to the reaction in toluene that require a high concentration of TFA and longer reaction time. Higher concentration of TFA in toluene reduces the reaction time but under these conditions, significant degradation and E/Z-isomerization of α-cryptoxanthin and β-cryptoxanthin is observed. The identity of individually isolated carotenoids from this reaction was established from their UV-Visible, MS, and $^1$H-NMR spectra.

TABLE 6

The relative composition of carotenoids in the products of the
reaction of anhydroluteins with trifluoroacetic acid (TFA) and triethylsilane
(Et₃SiH) in various solvents.*

| Anhydroluteins, 0.234 g, (80% pure) ≈ 0.187 g 0.34 mmol Containing 6–10% Zeaxanthin | Et₃SiH (mmol) | TFA (mmol) Reaction Time (h) | Zeaxanthin (All-E + 9Z + 13Z) (recovered) % | Anhydroluteins (All-E + Z) % | α-Cryptoxanthin (All-E + Z) % | β-Cryptoxanthin (All-E + Z) % | Total Weight (g) & % yield of Carotenoids |
|---|---|---|---|---|---|---|---|
| Solvent | | | | | | | |
| Dichloromethane | 0.94 | 1.30  2.5 h | 15.3 | 27.1 | 16.8 | 40.8 | 132 (70%) |
| Toluene | 0.94 | 2.60  6 h | 12.5 | 10.3 | 35.5 | 41.7 | 113 (60%) |
| Toluene | 0.94 | 2.98  6 h | 26.7 | 23.2 | 29.8 | 20.3 | 102 (55%) |
| Toluene | 0.94 | 4.22  2.5 h | 13.3 | 18.7 | 24.6 | 43.4 | 88 (47%) |

*In all experiments, TFA was added to a solution of anhydroluteins and triethylsilane in 20 ml of the solvent under an atmosphere of nitrogen at ambient temperature and the course of the reaction was followed by HPLC.

Therefore, in a preferred embodiment, the invention relates to a method of converting a mixture of anhydroluteins I, II, and III containing about 6–10% (3R,3'R)-zeaxanthin to a mixture of (3R,6'R)-α-cryptoxanthin and (3R)-β-cryptoxanthin in the presence of a strong acid and a hydride ion donor in an organic solvent comprising:

a) dissolving (3R,3'R,6'R)-lutein containing about 5–7% (3R,3'R)-zeaxanthin in a chlorinated solvent (dichloromethane, 1,2-dichloromethane) or toluene and adding triethylsilane (preferably 2.76 equivalent) under an inert atmosphere to obtain a mixture;

b) depending on the nature of the solvent, adding appropriate amount of TFA to the mixture at ambient temperature to promote the ionic hydrogenation reaction and obtain a crude product;

c) neutralizing the acid in the crude product by a addition of an inorganic or organic base solution of, e.g., sodium or potassium hydrogen carbonate;

d) distilling off the chlorinated solvent under reduced pressure e.g., with gradual displacement with a higher boiling alcohol, preferably 2-propanol and evaporating most of the alcohol under reduced pressure until carotenoids crystallize out from aqueous alcohol;

e) collecting the crystals e.g., by filtration or centrifugation and washing the crystalline product with a small volume of acetone; and f) drying the final product e.g., at 60° C. under high vacuum to obtain a mixture of carotenoids.

The invention further relates to a process for separating the Z(cis)-isomers of carotenoids from their all-E(trans)-compounds by washing the above dried mixture of carotenoids with a $C_5$–$C_7$ hydrocarbon or petroleum ether at 0° C. or lower (0° C. to −20° C.) to remove the Z-isomers and obtain a crystalline product comprising of predominantly all-E isomers of (3R,6'R)-α-cryptoxanthin, (3R)-β-cryptoxanthin, anhydroluteins as well as a high concentration of the unreacted (3R,3'R)-zeaxanthin.

Reactions of (3R,3'R,6'R)-lutein with $NaCNBH_3$/Zinc Halide ($ZnBr_2$ or $ZnI_2$). The reaction of (3R,3'R,6'R)-lutein with sodium cyanoborohydride ($NaCNBH_3$)/zinc iodide ($ZnI_2$) proceeds smoothly in dichloromethane and 1,2-dichloroethane at room temperature to selectively give ≈90% yield of (3R,6'R)-α-cryptoxanthin within 1–2 hours. This reaction gives predominantly the all-E isomer of (3R,6'R)-β-cryptoxanthin as opposed to the reaction of lutein with TFA/triethylsilane which is accompanied by significant E/Z-stereoisomerization. The reactions in tert-butyl methyl ether (TBME) also gives ≈90% yield of (3R,6'R)-α-cryptoxanthin but longer reaction time of up to 5 h is needed. In tetrahydrofuran (THF) or ethyl ether the reaction does not proceed. Similarly, no reaction is observed in methanol. Zinc bromide also reacts with lutein and $NaCNBH_3$ in dichloromethane to give approximately 75% of (3R,6'R)-α-cryptoxanthin. However, the reaction with zinc chloride and $NaCNBH_3$ results in a poor yield after 24 hours. The 5–7% of zeaxanthin that is present in the starting material does not react with $NaCNBH_3/ZnI_2$ or $NaCNBH_3/ZnBr_2$ and can be fully recovered in the product.

A summary of these reactions is shown in Table 7. The identity of the isolated (3R,6'R)-α-cryptoxanthin obtained from these reactions was established from its UV-Visible, MS, and ¹H-NMR spectra.

TABLE 7

Summary of the reactions of lutein (containing 5–7% zeaxanthin) with sodium cyanoborohydride and zinc iodide in various solvents.*

| Lutein, 0.300 g (85%) ≈ 0.255 g, 0.448 mmol | $ZnX_2$ X = I, Br, Cl (mmol) | $NaCNBH_3$ (mmol) | Zeaxanthin (all-E + Z) Recovered (g) & % relative distribution | α-cryptoxanthin (all-E + Z) (g) & % relative distribution | Total Weight of crude product (g) & % yield of α-cryptoxanthin |
|---|---|---|---|---|---|
| Solvent Reaction Time, h | | | | | |
| Dichloromethane 1 h | $ZnI_2$ 1.80 | 3.36 | 0.015 g 6.5% | 0.222 g 93.5% | 0.300 g 90% |
| Dichloromethane 2 h | ZnBr2 2.66 | 3.36 | 0.017 g 8.1% | 0.186 91.9% | 0.300 75% |
| Dichloromethane 24 h | $ZnCl_2$ 3.27 | 3.36 | 0.015 g 8.0% & Unreacted Lutein (66.0%) | 0.064 g 26.0% | 0.30 26% |
| 1,2-Dichloroethane 1 h | $ZnI_2$ 1.80 | 3.36 | 0.015 g 6.5% | 0.222 g 93.5% | 0.290 g 90% |
| Tert-butyl methyl ether (TBME) 5 h | $ZnI_2$ 1.80 | 3.36 | 0.015 g 6.5% | 0.222 g 93.5% | 0.300 g 90% |

*In all experiments, sodium cyanoborohydride was added to a solution of (3R, 3'R, 6'R)-lutein in 20 ml of the solvent followed by the addition of zinc iodide. All reactions were conducted at room temperature under an atmosphere of nitrogen and the course of the reaction was followed by TLC and HPLC.

The work-up of this reaction is quite simple and consists of the filtration of the product through Celite (filter aid) and evaporation of the solvent with simultaneous displacement with a higher boiling alcohol (e.g., methanol, ethanol, 2-propanol) at atmospheric pressure followed by removal of most of the alcohol under reduced pressure until the product crystallizes out from aqueous alcohol. Therefore the invention relates to a method of converting (3R,3'R,6'R)-lutein containing (3R,3'R)-zeaxanthin to (3R,6'R)-α-cryptoxanthin, comprising:

a) dissolving (3R,3'R,6'R)-lutein containing (3R,3'R)-zeaxanthin in a chlorinated solvent and adding an effective amount of a metal hydride, then adding an effective amount of a zinc halide to give a mixture;

b) stirring the mixture;

c) filtering the mixture;

d) evaporating the solvent and obtaining a crystalline product; and e) collecting the crystalline product.

In a preferred embodiment, the invention relates to method of converting (3R,3'R,6'R)-lutein containing 5–7% (3R,3'R)-zeaxanthin to (3R,6'R)-α-cryptoxanthin, comprising:

a) dissolving (3R,3'R,6'R)-lutein containing about 5–7% (3R,3'R)-zeaxanthin in a volume (e.g., 6.7 ml solvent/100 mg lutein) of dichloromethane or 1,2-dichloromethane or an ether (TBME) and adding about 7.5 equivalent of metal hydride, e.g. sodium cyanoborohydride, followed by addition of 4 equivalent of zinc iodide or zinc bromide under an inert atmosphere to obtain a mixture;

b) stirring the above mixture at ambient temperature, preferably, under an atmosphere of nitrogen or argon for about one to five hours to obtain a crude product;

c) filtering the crude product, e.g. through Celite (filter aid) and washing the filter with additional solvent until all the color is removed;

d) evaporating the combined solvent under atmospheric or reduced pressure with displacement with a higher boiling alcohol (methanol, ethanol, or 2-propanol) until the product crystallizes out;

e) collecting the crystals by filtration or on a centrifuge and washing the crystals with alcohol or acetone;

f) drying the crystals under high vacuum, e.g. at 60° C. to obtain a mixture of recovered (3R,3'R)-zeaxanthin and (3R, 6'R)-α-cryptoxanthin.

Reactions of (3R,3'R,6'R)-lutein with sodium (trifluoroacetoxy)borohydride $Na[BH_3(OCOCF_3)]$/zinc halide ($ZnBr_2$ or $ZnI_2$). Sodium (trifluoroacetoxy) borohydride reacts with lutein in the presence of zinc bromide in a chlorinated solvent (dichloromethane or 1,2-dichloroethane) at 0–5° C. to give (3R,6'R)-α-cryptoxanthin nearly quantitatively. In a typical experiment, a solution of lutein (0.45 mmol) in dichloromethane or 1,2-dichloroethane (20 ml) kept at 0° C. under nitrogen is treated with zinc bromide (0.58 mmol) followed by sodium (trifluoroacetoxy)borohydride (1.82 mmol). Sodium (trifluoroacetoxy)-borohydride is prepared by slowly adding trifluoroacetic acid (1.82 mmol) to a suspension of sodium borohydride (1.90 mmol) in THF (2 ml) at 10–15° C. and under an inert atmosphere such as nitrogen or argon. The mixture is then stirred at room temperature for 20 minutes. In the preparation of sodium (trifluoroacetoxy)borohydride, the starting materials (TFA and sodium borohydride) should be weighed accurately to avoid the presence of unreacted TFA in the product which can cause dehydration of lutein. The reaction takes approximately 4 to 5 h at 0–5° C. to result in complete conversion of lutein to (3R,6'R)-α-cryptoxanthin. The work up consists of adding a 2% solution of sodium bicarbonate (10 ml) to destroy the excess of the borohydride. After separating, drying, and filtering the organic layer, the solvent is evaporated with simultaneous displacement with a higher boiling alcohol (methanol, ethanol, 2-propanol) at atmospheric pressure. This is followed by removal of most of the alcohol under reduced pressure until the product crystallizes out from alcohol. This reaction also works with zinc iodide under exactly the same conditions; however, the product consist of approximately 57% (3R,6'R)-α-cryptoxanthin and 43% of anhydroluteins which are formed as side products. The allylic deoxygenation of lutein with sodium (trifluoroacetoxy)borohydride and a zinc halide (zinc bromide or zinc iodide) in non-chlorinated solvents (e.g. tert-butyl methyl ether, diglyme, 1,2-dimethoxyethane, diethyl ether, THF, DMF) did not work.

Therefore the invention relates to a method of converting (3R,3'R,6'R)-lutein (e.g. containing 5–7% (3R,3'R)-zeaxanthin) to (3R,6'R)-α-cryptoxanthin comprising reacting (3R,3'R,6'R)-lutein, sodium (trifluoroacetoxy)borohydride and a zinc halide, preferably zinc bromide or zinc iodide, in a chlorinated solvent (e.g. dichloromethane or 1,2-dichloroethane), preferably at 0–5° C. In a preferred embodiment, the reaction comprises:

a) dissolving (3R,3'R,6'R)-lutein containing approximately 5–7% (3R,3'R)-zeaxanthin in an appropriate volume (about 6.7 ml solvent/100 mg lutein) of a chlorinated solvent (e.g. dichloromethane or 1,2-dichloromethane) and cooling the mixture to about 0° C.;

b) adding about 1.3 equivalent of zinc bromide or zinc iodide followed by addition of about 4 equivalent of freshly prepared sodium (trifluoroacetoxy)borohydride under an inert atmosphere to obtain a mixture;

c) stirring the mixture at 0° C. under an atmosphere of nitrogen or argon for up to about five hours to obtain a crude product;

d) adding an aqueous solution of a base (e.g. aqueous sodium bicarbonate) to destroy the excess of borohydride, separating the organic layer and drying it (e.g. over sodium sulfate);

e) evaporating the organic solvent e.g. at atmospheric pressure by gradual displacement with a higher boiling alcohol (e.g. methanol, ethanol or 2-propanol) and evaporating the alcohol under reduced pressure until the product crystallizes out;

f) collecting the crystals, e.g. by filtration or on a centrifuge and washing the crystals with alcohol or acetone;

g) drying the crystals e.g. under high vacuum at 60° C. to obtain a mixture of recovered (3R,3'R)-zeaxanthin and (3R,6'R)-α-cryptoxanthin.

Reactions of (3R,3'R,6'R)-lutein with $Me_3N.BH_3/AlCl_3$ or $Me_2NH.BH_3/AlCl_3$ in non-chlorinated solvents, (3R,3'R,6'R)-Lutein reacts with borane-trimethylamine ($Me_3N.BH_3$) or borane-dimethylamine ($Me_2NH.BH_3$) complexes in the presence of aluminum chloride at room temperature in tetrahydrofuran (THF) or ethylene glycol dimethyl ether to give # 90% yield of (3R,6'R)-α-cryptoxanthin within 1–2 hours. The 5–7% of (3R,3'R)-zeaxanthin that is present in the starting material does not react with $Me_3N.BH_3/AlCl_3$ or $Me_2NH.BH_3/AlCl_3$ and can be fully recovered in the product. In a typical experiment, a solution of lutein (0.448 mmol) in THF or ethylene glycol dimethyl ether (30 ml) is first treated with 2.69 mmol of $Me_3N.BH_3$ or $Me_2NH.BH_3$ and this is followed by the addition of $AlCl_3$ (1.03 mmol). The mixture is then stirred at ambient temperature under an inert atmosphere (e.g. nitrogen or argon) for 1–2 hours.

The work-up consists of adding 2% solution of sodium bicarbonate (10 ml) and 10 ml of a second solvent (only in case of THF) such as ethyl acetate or a $C_4$–$C_6$-ether (diethyl ether, diisopropyl ether, TBME, 1,2-dimethoxyethane). When ethylene glycol dimethyl ether is used as solvent in the reaction, the use of the second solvent during work up can be omitted. Most of the organic layer is removed under reduced pressure and (3R,6'R)-α-cryptoxanthin is crystallized from an alcohol. Therefore the invention relates to a method of converting (3R,3'R,6'R)-lutein (e.g. containing (3R,3'R)-zeaxanthin) to (3R,6'R)-α-cryptoxanthin, comprising reacting (3R,3'R,6'R)-lutein, $Me_3N.BH_3$ or $Me_2NH.BH_3$ and aluminum chloride in an ether, preferably, THF or ethylene glycol dimethyl ether (1,2-dimethoxyethane) at ambient temperature. In a preferred embodiment, the reaction comprises:

a) dissolving (3R,3'R,6'R)-lutein containing (3R,3'R)-zeaxanthin in an appropriate volume (about 10 ml solvent/100 mg lutein) of THF or ethylene glycol dimethyl ether (1,2-dimethoxyethane) and adding 6 mol equivalent of $Me_3N.BH_3$ or $Me_2NH.BH_3$, then adding 2.3 mol equivalent of aluminum chloride to obtain a mixture;

b) stirring the mixture at ambient temperature under an inert atmosphere (nitrogen or argon) for 1–2 hours;

c) adding an aqueous solution of a base (e.g. sodium bicarbonate and a second organic solvent (only in case of THF) such as ethyl acetate or an ether, separating the organic layer and drying it (e.g. over sodium sulfate);

d) evaporating most of the organic solvent under reduced pressure and crystallizing the residue from an alcohol;

e) collecting the crystals, e.g. by filtration or on a centrifuge and washing the crystals with an alcohol or acetone;

f) drying the crystals e.g. under high vacuum at 60° C. to obtain a mixture of recovered (3R,3'R)-zeaxanthin and (3R,6'R)-α-cryptoxanthin.

Reactions of (3R,3'R,6'R)-lutein with $LiClO_4/Et_3SiH$. In another approach, the invention relates to a method of converting the 85% commercially available or highly purified (3R,3'R,6'R)-lutein containing (3R,3'R)-zeaxanthin and mixtures thereof to a mixture of (3R,6'R)-α-cryptoxanthin and (3R,6'R)-anhydrolutein I in the presence of an ethereal solution of $LiClO_4$/hydride ion donor. In a preferred embodiment, this method comprises:

a) reacting (3R,3'R,6'R)-lutein containing about 5–7% (3R,3'R)-zeaxanthin with lithium perchlorate-ether solution in the presence of triethylsilane at room temperature under an inert atmosphere such as nitrogen or argon to obtain a crude product;

b) partitioning the crude product into water to give an organic layer and an aqueous layer;

c) separating the organic layer and displacing the ether with a second solvent comprising higher boiling alcohol or $C_5$–$C_7$ hydrocarbon by distillation and evaporating the second solvent under reduced pressure until anhydrolutein I and (3R,6'R)-α-cryptoxanthin crystallize out;

d) collecting the crystals, e.g., by filtration or on a centrifuge;

e) washing the crystals, e.g., with small volume of acetone; and f) drying the crystals, e.g., under high vacuum at 60° C. to obtain a mixture of anhydrolutein I and (3R,6'R)-α-cryptoxanthin.

In a preferred embodiment, the lithium perchlorate is added as an about 3 M solution in diethlyether. Also in a preferred embodiment, the ether is displaced by addition of the alcohol or hydrocarbon and by distillation at atmospheric pressure.

As used herein, the term "about" means that number referred to as having "about" comprises the recited number plus or minus up to 10% of that number. For example, "about 5 hours" includes 4.5 to 5.5 hours. "About 0° C." includes –10° C., 0° C. and +10° C.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLE 1

Conversion of (3R,3'R,6'R)-Lutein (85%) to (3R, 6'R)-α-Cryptoxanthin and (3R)-β-Cryptoxanthin with Trifluoroacetic Acid (TFA) and Triethylsilane (Et$_3$SiH) in Dichloromethane A solution of (3R,3'R,6'R)-lutein (0.300 g of 85% pure ≈0.255 g, 0.448 mmol)) in dichloromethane (25 ml) was first treated with triethylsilane (0.150 ml, 0.109 g, 0.94 mmol) followed by trifluoroacetic acid (0.12 ml, 0.178 g, 1.56 mmol). The mixture was stirred at ambient temperature under an atmosphere of nitrogen and the course of the reaction was followed by HPLC. After 8 h, the product was treated with 5% solution of sodium bicarbonate (15 ml) and stirred for 5 minutes. The mixture was distilled at atmospheric pressure by gradual displacement of dichloromethane (b.p.=40° C.) with 2-propanol (b.p.=82.4° C.). When nearly all of the dichloromethane was removed, the alcohol was distilled off under reduced pressure until carotenoids began to crystallize from aqueous alcohol. The mixture was allowed to cool down to room temperature and the crystals were removed on a centrifuge. The aqueous layer was removed and the remaining crystals were treated with 10 ml of acetone and stirred for a few minutes. The solvent was removed by centrifugation and the crystalline product was dried under high vacuum at 60° C. to give a red solid (0.263 g). This was shown by HPLC to contain 223 mg (90% yield) of total carotenoids consisting of a mixture of (3R,6'R)-α-cryptoxanthin (25.2%), (3R)-β-cryptoxanthin (39.1%), unreacted (3R,6'R)-anhydroluteins (18.7%), (all-E, 3R,3'R)-zeaxanthin (10.5%), (9Z, 3R,3'R)-zeaxanthin (3%), and (13Z, 3R,3'R)-zeaxanthin (3.5%). The crude product was crystallized with hexane (6 ml) at low temperature (0° to −20° C.) to give orange crystals consisting of a mixture of carotenoids. The relative composition of carotenoids in the mother liquor from crystallization was: (3R,6'R)-α-cryptoxanthin (32%), (3R)-β-cryptoxanthin (51.6%), anhydroluteins (14.4%), and (3R,3'R)-zeaxanthin (2%). The orange crystals were removed on a centrifuge and dried under high vacuum at 60° C. The relative distribution of carotenoids in the solid was: (3R,6'R)-α-cryptoxanthin (18.5%), (3R)-β-cryptoxanthin (26.5%), anhydroluteins (11.4%), (all-E, 3R,3'R)-zeaxanthin (33.5%), (9Z, 3R,3'R)-zeaxanthin (4.3%), and (13Z, 3R,3'R)-zeaxanthin (5.8%),

EXAMPLE 2

Conversion of (3R,3'R,6'R)-Lutein (85%) to (3R, 6'R)-α-Cryptoxanthin and (3R)-β-Cryptoxanthin with Trifluoroacetic Acid (TFA) and Triethylsilane (Et$_3$SiH) in 1,2-Dichloroethane A solution of (3R,3'R,6'R)-lutein (0.300 g of 85% pure ≈0.255 g, 0.448 mmol)) in 1,2-dichloroethane (25 ml) was first treated with triethylsilane (0.150 ml, 0.109 g, 0.94 mmol) followed by trifluoroacetic acid (0.12 ml, 0.178 g, 1.56 mmol). The mixture was stirred at ambient temperature under an atmosphere of nitrogen and the course of the reaction was followed by HPLC. After 8 h, the product was treated with 5% solution of sodium bicarbonate (15 ml) and stirred for 5 minutes. Most of 1,2-dichloroethane (b.p.=83° C.) was distilled under reduced pressure. 2-Propanol (20 ml) was added and distillation continued until carotenoids began to crystallize from aqueous alcohol. The mixture was allowed to cool down to room temperature and the crystals were removed by centrifugation. The aqueous layer was removed and the remaining crystals were treated with 10 ml of acetone and stirred for a few minutes. The solvent was removed on a centrifuge and the crystalline product was dried under high vacuum at 60° C. to give a red solid (0.250 g). This was shown by HPLC to contain 216 mg (87% yield) of total carotenoids consisting of a mixture of (3R,6'R)-α-cryptoxanthin (28.2%), (3R)-β-cryptoxanthin (26.8%), unreacted (3R,6'R)-anhydroluteins (30.8%), and recovered (all-E+Z 3R,3'R)-zeaxanthin (14.2%).

EXAMPLE 3

Separation and Purification of Carotenoids from a Mixture of (3R,6'R)-α-Cryptoxanthin, (3R)-β-Cryptoxanthin, Anhydroluteins, and (3R,3'R)-Zeaxanthin by Column Chromatography A flash column (20 cm 1×3.5 cm i.d.) was packed under slight pressure with n-silica gel (40 μm particle size) employing a mixture of hexane (90%) and acetone (10%). 0.3 g of a crude mixture of (3R,6'R)-α-cryptoxanthin, (3R)-β-cryptoxanthin, anhydroluteins, and (3R,3'R)-zeaxanthin obtained from reaction of (3R,3'R,6'R)-lutein with TFA/Et$_3$SiH (example 1 or 2) was loaded onto the column using a 1/1 mixture of hexane and acetone. The mixture of carotenoids was eluted with hexane/acetone (9/1). Three major colored bands were collected. In the order of elution these were; 1) a pure mixture of (3R,6'R)-α-cryptoxanthin and (3R)-β-cryptoxanthin, 2) a mixture of anhydrolutein I, II, and III, and 3) (3R,3'R)-zeaxanthin. The solvents were evaporated under reduced pressure and the pure carotenoids were dried under high vacuum at 60° C.

EXAMPLE 4

Conversion of (3R,3'R,6'R)-Lutein (85% pure) to Anhydroluteins I, II, and III with Sulfuric Acid in Tetrahydrofuran (THF)

(3R,3'R,6'R)-Lutein (3.36 g of 85% pure ≈2.86 g, 5.03 mmol)) in 150 ml of a tetrahydrofuran (THF) was allowed to react with 50% (v/v) sulfuric acid (10 ml) at room temperature under nitrogen for 4 h. The product was slowly treated with 4 M potassium hydroxide (50 ml) until the pH was about 5 or 6. The mixture was then treated with a 5% solution of sodium bicarbonate (5 ml) and triethylamine (1 ml) to neutralize the remainder of the acid. Most of THF was evaporated under reduced pressure, 2-Propanol (50 ml) was added and distillation continued until anhydroluteins crystallized from aqueous alcohol. The crystals were removed on a centrifuge, washed with 30 ml of acetone, and dried under high vacuum at 60° C. to give 3.18 g of an orange product which was shown by HPLC to contain 2.54 g of a mixture of anhydroluteins (92% yield) and recovered zeaxanthin. The relative distribution of carotenoids in this product was: (3R,6'R)-anhydrolutein I (58%), anhydrolutein II (8.8%), all-E-anhydrolutein II (18.4%), Z-anhydrolutein III (7.9%), and (3R,3'R)-zeaxanthin (6.9%). This mixture was used in subsequent reactions with TFA/Et$_3$SiH without further purification.

EXAMPLE 5

Conversion of (3R,3'R,6'R)-Lutein (85% pure) to Anhydroluteins I, II, and III with Trifluoroacetic Acid (3R,3'R,6'R)-Lutein (1 g of 85% pure ≈0.85 g, 1.49 mmol)) in 150 ml of chloroform was allowed to react with trifluoroacetic acid (0.2 ml) at room temperature overnight (21 h). The product was treated with a 5% solution of sodium bicarbonate (50 ml) and triethylamine (0.2 ml). Most of the chloroform was evaporated under reduced pressure. 2-Propanol was added and distillation continued until anhydroluteins crystallized from aqueous alcohol. The crystals were removed on a centrifuge, washed with 15 ml of acetone, and dried under high vacuum at 60° C. to give 0.96 g of an orange product which was shown by HPLC to contain 0.77 g of a mixture of anhydroluteins (94% yield) and unreacted zeaxanthin. The relative distribution of carotenoids in this product was: (3R,6'R)-anhydrolutein I (74.9%), anhydrolutein II (9%), all-E-anhydrolutein III (5.3%), and (3R,3'R)-zeaxanthin (10.8%).

EXAMPLE 6

Conversion of Anhydroluteins I, II, and III to (3R, 6'R)-α-Cryptoxanthin and (3R)-β-Cryptoxanthin in Dichloromethane A solution of anhydroluteins I, II, and III (0.234 g, 80% ≈0.187 g, 0.34 mmol) in dichloromethane (20 ml) was first treated with triethylsilane (0.150 ml, 0.109 g, 0.94 mmol) followed by trifluoroacetic acid (0.100 ml, 0.148 g, 1.30 mmol). The mixture was stirred at ambient temperature under an atmosphere of nitrogen and the course of the reaction was followed by HPLC. After 2.5 h, the product was treated with 5% solution of sodium bicarbonate (15 ml) and stirred for 5 minutes. The mixture was distilled at atmospheric pressure by gradual displacement of dichloromethane (b.p.=40° C.) with 2-propanol (b.p.=82.4° C.). When nearly all of the dichloromethane was removed, the alcohol was distilled off under reduced pressure until carotenoids began to crystallize from aqueous alcohol. The mixture was allowed to cool down to room temperature and the crystals were removed on a centrifuge. The aqueous layer was removed and the remaining crystals were treated with 10 ml of acetone and stirred for a few minutes. The solvent was removed on a centrifuge and the crystalline product was dried under high vacuum at 60° C. to give a red solid (0.188 g). This was shown by HPLC to contain 132 mg (70% yield) of total carotenoids consisting of a mixture of (3R,6'R)-α-cryptoxanthin (16.8%), (3R)-β-cryptoxanthin (40.8%), unreacted (3R,6'R)-anhydroluteins (27.1%), and (3R,3'R)-zeaxanthin (15.3%).

EXAMPLE 7

Conversion of Anhydroluteins I, II, and III to (3R, 6'R)-α-Cryptoxanthin and (3R)-β-Cryptoxanthin in Toluene A solution of anhydroluteins I, II, and III (0.234 g, 80% ≈0.187 g, 0.34 mmol) in toluene (20 ml) was first treated with triethylsilane (0.150 ml, 0.109 g, 0.94 mmol) followed by trifluoroacetic acid (0.200 ml, 0.296 g, 2.60 mmol). The mixture was stirred at ambient temperature under an atmosphere of nitrogen and the course of the reaction was followed by HPLC. After 6 h, the product was treated with 5% solution of sodium bicarbonate (15 ml) and stirred for 5 minutes. Most of toluene was removed by distillation under reduced pressure. 2-Propanol (20 ml) was added and distillation continued until carotenoids began to crystallize from aqueous alcohol. The mixture was allowed to cool down to room temperature and the crystals were removed on a centrifuge. The aqueous layer was removed and the remaining crystals were treated with 10 ml of acetone and stirred for a few minutes. The solvent was removed on a centrifuge and the crystalline product was dried under high vacuum at 60° C. to give a red solid (0.188 g). This was shown by HPLC to contain 113 mg (60% yield) of total carotenoids consisting of a mixture of (3R,6'R)-α-cryptoxanthin (35.5%), (3R)-β-cryptoxanthin (41.7%), unreacted (3R, 6'R)-anhydroluteins (10.3%), and (3R,3'R)-zeaxanthin (12.5%),

EXAMPLE 8

Selective Deoxygenation of (3R,3'R,6'R)-Lutein (85%) to (3R,6'R)-α-Cryptoxanthin with Sodium Cyanoborohydride (NaCNBH$_3$) and Zinc Iodide (ZnI$_2$) in Dichloromethane A solution of (3R,3'R,6'R)-lutein (0.300 g of 85% pure ≈0.255 g, 0.448 mmol)) in dichloromethane (20 ml) was treated with sodium cyanoborohydride (0.211 g, 3.36 mmol) and zinc iodide (0.575 g, 1.80 mmol). The mixture was stirred at ambient temperature under an atmosphere of nitrogen and the course of the reaction was followed by HPLC and TLC (hexane/acetone=4/1; lutein (R$_f$=0.18), α-cryptoxanthin (R$_f$=0.51)). After 1 hour, the product was filtered through Celite (filter aid) and the Celite was washed with dichloromethane until all the color was removed. The solvent was distilled at atmospheric pressure by gradual displacement of dichloromethane (b.p.=40° C.) with 2-propanol (b.p.=82.4° C.). After nearly all the dichloromethane was removed, most of the alcohol was evaporated under reduced pressure until α-cryptoxanthin crystallized. The crystals were removed on a centrifuge, washed with alcohol (10 ml), and dried under high vacuum at 60° C. to give 0.3 g of an orange solid which was shown by HPLC to consist of a mixture of α-cryptoxanthin (0.222 g, 0.39 mmol, 90%) and recovered zeaxanthin (0.015 g, all-E (73%), 9Z (6%), 13Z (21%)). The concentration of α-cryptoxanthin determined by spectrophotometric measurement in hexane (E1%=2636 at λmax=444 nm), was also in close agreement with the HPLC data.

EXAMPLE 9

Selective Deoxygenation of (3R,3'R,6'R)-Lutein (85%) to (3R,6'R)-α-Cryptoxanthin with Sodium Cyanoborohydride (NaCNBH$_3$) and Zinc Iodide (ZnI$_2$) in 1,2-Dichloroethane A solution of (3R,3'R,6'R)-lutein (0.300 g of 85% pure ≈0.255 g, 0.448 mmol)) in 1,2-dichloroethane (20 ml) was treated with sodium cyanoborohydride (0.211 g, 3.36 mmol) and zinc iodide (0.575 g, 1.80 mmol). The mixture was stirred at ambient temperature under an atmosphere of nitrogen and the course of the reaction was followed by HPLC and TLC (hexane/acetone=4/1; lutein (R$_f$=0.18), α-cryptoxanthin (R$_f$=0.51)). After 1 hour, the product was filtered through Celite (filter aid) and the Celite was washed with more 1,2-dichloroethane until all the color was removed. The solvent was distilled at atmospheric pressure by gradual displacement of dichloromethane (b.p.=40° C.) with 2-propanol (b.p.=82.4° C.). After nearly all the dichloromethane was removed, most of the alcohol was evaporated under reduced pressure until α-cryptoxanthin crystallized. The crystals were removed on a centrifuge, washed with alcohol (10 ml), and dried under high vacuum at 60° C. to give 0.3 g of an orange solid which was shown by HPLC to consist of a mixture of α-cryptoxanthin (0.222 g, 0.39 mmol, 90%) and recovered zeaxanthin (0.015 g, all-E (92%), 9Z (2%), 13Z (6%)). The concentration of α-cryptoxanthin determined by spectrophotometric measurement in hexane (E1%=2636 at λmax=444 nm), was also in close agreement with the HPLC data.

EXAMPLE 10

Selective Deoxygenation of (3R,3'R,6'R)-Lutein (85%) to (3R,6'R)-α-Cryptoxanthin with Sodium Cyanoborohydride (NaCNBH$_3$) and Zinc Iodide (ZnI$_2$) in tert-Butyl Methyl Ether (TBME)

A solution of (3R,3'R,6'R)-lutein (0.300 g of 85% pure ≈0.255 g, 0.448 mmol) in TBME (20 ml) was treated with sodium cyanoborohydride (0.211 g, 3.36 mmol) and zinc iodide (0.575 g, 1.80 mmol). The mixture was stirred at ambient temperature under an atmosphere of nitrogen and the course of the reaction was followed by HPLC and TLC (hexane/acetone=4/1; lutein ($R_f$=0.18), α-cryptoxanthin ($R_f$=0.51)). After 5 hour, the product was filtered through Celite (filter aid) and the Celite was washed with TBME until all the color was removed. The volume of TBME (b.p.=55–56° C.) was reduced to 10 ml by distillation under reduced pressure. 2-Propanol (20 ml) was added and distillation was continued under reduced pressure until the rest of the TBME was displaced with 2-propanol (b.p.=82.4° C.). Distillation of alcohol under reduced pressure continued until α-cryptoxanthin crystallized. The crystals were removed on a centrifuge, washed with alcohol, and dried under high vacuum at 60° C. to give 0.3 g of an orange solid which was shown by HPLC to consist of a mixture of α-cryptoxanthin (0.222 g, 0.39 mmol, 90%) and recovered zeaxanthin (0.015 g, all-E (96%), 9Z (1%), 13Z (3%)). The concentration of α-cryptoxanthin determined by spectrophotometric measurement in hexane (E1%=2636 at λmax=444 nm), was also in close agreement with the HPLC data.

EXAMPLE 11

Selective Deoxygenation of (3R,3'R,6'R)-Lutein (85%) to (3R,6'R)-α-Cryptoxanthin with Sodium (trifluoroacetoxy)borohydride Na(BH$_3$(OCOCF$_3$)) and Zinc Bromide (ZnBr$_2$) in Dichloromethane Preparation of Na(BH$_3$(OCOCF$_3$)). Trifluoroacetic acid (0.14 ml, 0.207 g, 1.82 mmol) was added dropwise with an airtight syringe to a suspension of sodium borohydride (0.072 g, 1.90 mmol) in THF (2 ml) cooled to 10–15° C. and maintained under an atmosphere of nitrogen. The mixture was stirred at room temperature for 10 minutes to give a clear solution.

(3R,3'R,6'R)-Lutein (0.300 g of 85% pure ≈0.255 g, 0.448 mmol)) was dissolved in dichloromethane (20 ml) in a three-necked flask equipped with a thermometer, nitrogen inlet mid outlet and the solution was cooled in an ice-bath to 0° C. under an atmosphere of nitrogen. The mixture was treated with zinc bromide (0.130 g, 0.577 mmol) and then the above sodium (trifluoroacetoxy)borohydride (1.82 mmol) was added all at once under nitrogen at 0–5° C. The mixture was stirred at this temperature and the course of the reaction was followed by HPLC and TLC (hexane/acetone 4/1; lutein ($R_f$=0.18), α-cryptoxanthin ($R_f$=0.51)). After 5 hours, the ice-bath was removed and the product was treated with 10 ml of 2% sodium bicarbonate and allowed to stir at ambient temperature for 10 minutes. The organic layer was removed, dried over sodium sulfate and the solvent was distilled at atmospheric pressure by gradual displacement of dichloromethane (b.p.=40° C.) with 2-propanol (b.p.=82.4° C.). After nearly all the dichloromethane was removed, most of the alcohol was evaporated under reduced pressure until α-cryptoxanthin crystallized. The crystals were removed on a centrifuge, washed with alcohol (10 ml), and dried under high vacuum at 60° C. to give 0.3 g of an orange solid which was shown by HPLC to consist of a mixture of α-cryptoxanthin (0.234 g, 0.39 mmol, 95%) and recovered zeaxanthin (0.018 g, all-E (80%), 9Z (5%), 13Z (15%)).

EXAMPLE 12

Selective Deoxygenation of (3R,3'R,6'R)-Lutein (85%) to (3R,6'R)-α-Cryptoxanthin with Sodium (trifluoroacetoxy)borohydride Na(BH$_3$(OCOCF$_3$)) and Zinc Iodide (ZnI$_2$) in Dichloromethane Preparation of Na(BH$_3$(OCOCF$_3$)). Trifluoroacetic acid (0.14 ml, 0.207 g, 1.82 mmol) was added dropwise with an airtight syringe to a suspension of sodium borohydride (0.072 g, 1.90 mmol) in THF (2 ml) cooled to 10–15° C. and maintained under an atmosphere of nitrogen. The mixture was stirred at room temperature for 10 minutes to give a clear solution.

(3R,3'R,6'R)-Lutein (0.300 g of 85% pure ≈0.255 g, 0.448 mmol)) was dissolved in dichloromethane (20 ml) in a three-necked flask equipped with a thermometer, nitrogen inlet and outlet and the solution was cooled in an ice-bath to 0° C. under an atmosphere of nitrogen. The mixture was treated with zinc iodide (0.186 g, 0.583 mmol) and then the above sodium (trifluoroacetoxy)borohydride (1.82 mmol) was added all at once under nitrogen at 0–5° C. The mixture was stirred at this temperature and the course of the reaction was followed by HPLC and TLC (hexane/acetone=4/1; lutein ($R_f$=0.18), α-cryptoxanthin ($R_f$=0.51). After 5 hours, the ice-bath was removed and the product was treated with 10 ml of 2% sodium bicarbonate and allowed to stir at ambient temperature for 10 minutes. The organic layer was removed, dried over sodium sulfate and the solvent was distilled at atmospheric pressure by gradual displacement of dichloromethane (b.p.=40° C.) with 2-propanol (b.p.=82.4° C.). After nearly all the dichloromethane was removed, most of the alcohol was evaporated under reduced pressure until α-cryptoxanthin crystallized. The crystals were removed on a centrifuge, washed with alcohol (10 ml), and dried under high vacuum at 60° C. to give 0.3 g of an orange solid which was shown by HPLC to consist of a mixture of anhydro-luteins (0.100 g, 0.18 mmol, 43%) and α-cryptoxanthin (0.134 g, 0.243 mmol, 57%) as well as recovered zeaxanthin (0.015 g).

EXAMPLE 13

Selective Deoxygenation of (3R,3'R6'R)-Lutein (85%) to (3R,6'R)-α-Cryptoxanthin with Borane-Trimethylamine (Me$_3$N.BH$_3$) Complex and Aluminum Chloride (AlCl$_3$) in Tetrahydrofuran (THF)

A solution of (3R,3'R,6'R)-lutein (0.300 g of 85% pure ≈0.255 g, 0.448 mmol)) in THF (30 ml) was first treated with borane-trimethylamine (Me$_3$N.BH$_3$) complex (0.196 g, 2.69 mmol) followed by aluminum chloride (0.137 g, 1.03 mmol). The mixture was stirred at ambient temperature under an atmosphere of nitrogen and the course of the reaction was followed by HPLC and TLC (hexane/acetone= 4/1; lutein ($R_f$=0.18), α-cryptoxanthin ($R_f$=0.51)). After 90 min, the product was treated with 15 ml of aqueous sodium bicarbonate and 30 ml of ethyl acetate. The organic layer was removed, dried over sodium sulfate, and most of the organic solvents were evaporated under reduced pressure until the product crystallized. Ethanol (10 ml) was added and the crystals of α-cryptoxanthin were removed on a centrifuge, washed with small amount of acetone (10 ml), and dried under high vacuum at 60° C. to give 0.3 g of an orange solid. This was shown by HPLC to consist of a mixture of α-cryptoxanthin (0.222 g, 0.39 mmol, 90%) and recovered zeaxanthin (0.015 g, all-E (73%), 9Z (6%), 13Z (21%)).

EXAMPLE 14

Selective Deoxygenation of (3R,3'R,6'R)-Lutein (85%) to (3R,6'R)-α-Cryptoxanthin with Borane-Trimethylamine ($Me_3N.BH_3$) Complex and Aluminum Chloride ($AlCl_3$) in Ethylene Glycol Dimethyl Ether (1,2-dimethoxyethane)

A solution of (3R,3'R,6'R)-lutein (0.300 g of 85% pure ≈0.255 g, 0.448 mmol)) in 1,2-dimethoxyethane (30 ml) was first treated with borane-trimethylamine ($Me_3N.BH_3$) complex (0.196 g, 2.69 mmol) followed by aluminum chloride (0.137 g, 1.03 mmol). The mixture was stirred at ambient temperature under an atmosphere of nitrogen and the course of the reaction was followed by HPLC and TLC hexane/acetone=4/1; lutein ($R_f$=0.18), α-cryptoxanthin ($R_f$=0.51)). After 90 min, the product was treated with 15 ml of aqueous sodium, bicarbonate. The organic layer was removed, dried over sodium sulfate, and most of the 1,2-dimethoxyethane was evaporated under reduced pressure until the product crystallized. Ethanol (10 ml) was added and the crystals of α-cryptoxanthin were removed on a centrifuge, washed with small amount of acetone (10 ml), and dried under high vacuum at 60° C. to give 0.3 g of an orange solid. This was shown by HPLC to consist of a mixture of α-cryptoxanthin (0.222 g, 0.39 mmol, 90%) and recovered zeaxanthin (0.015 g, all-E (73%), 9Z (6%), 13Z (21%)).

EXAMPLE 15

Conversion of (3R,3'R,6'R)-Lutein (85%) to (3R,6'R)-α-Cryptoxanthin and Anhydrolutein I with Lithium Perchlorate ($LiClO_4$)-Ethyl Ether and Triethylsilane ($Et_3SiH$)

A solution of (3R,3'R,6'R)-lutein (0.300 g of 85% pure ≈0.255 g, 0.448 mmol)) in ether (25 ml) was first treated with triethylsilane (0.300 ml, 0.218 g, 1.87 mmol) followed by addition of lithium perchlorate (8.00 g, 75.2 mmol). The solution immediately turned dark red and the temperature of the solution increased by 5° C. The mixture was stirred at ambient temperature under an atmosphere of nitrogen and the course of the reaction was followed by HPLC. After 24 h, water (30 ml) was added and the organic layer was removed. The mixture was distilled at atmospheric pressure by gradual displacement of ether (b.p.=37° C.) with hexane (b.p.=68° C.). When nearly all of the ether was removed, hexane was distilled off under reduced pressure until carotenoids began to crystallize from hexane. The mixture was allowed to cool down to room temperature and the crystals were removed on a centrifuge. The crystalline product was dried under high vacuum at 60° C. to give a red solid (0.6 g). This was shown by HPLC to contain 210 mg of total carotenoids consisting of a mixture of (3R,6'R)-α-cryptoxanthin (45%), all-E-anhydrolutein I (38.0%), Z-anhydrolutein I (8.4%), (all-E, 3R,3'R)-zeaxanthin (5.5%), (9Z, 3R,3'R)-zeaxanthin (1.5%), and (13Z, 3R,3'R)-zeaxanthin (1.6%).

Summary

Anhydroluteins I, II, and III, (3R,6'R)-α-cryptoxanthin, (3R)-β-cryptoxanthin, and (3R,3'R)-zeaxanthin are among the 12 major dietary carotenoids that are found in human serum, milk, major organs, and tissues. In view of the biological activity of carotenoids in the prevention of chronic diseases such as cancer, age-related macular degeneration, and cardiovascular disease, industrial production of a wide range of purified carotenoids is of great importance. While several dietary carotenoids, i.e. β-carotene, lutein, and lycopene, are commercially available as nutritional supplements and food coloring additives, the production of a wide range of other serum carotenoids has not yet received much attention. (3R,6'R)-α-Cryptoxanthin and (3R)-β-cryptoxanthin are among the rare carotenoids in nature and as a result extraction and isolation of these carotenoids from natural products on industrial scale is not economically viable.

According to preferred embodiments of the present invention commercially available (3R,3'R,6'R)-lutein undergoes selective allylic deoxygenation upon treatment with trifluoroacetic acid (TFA) and triethylsilane ($Et_3SiH$) in chlorinated solvents (dichloromethane, 1,2-dichloroethane) at ambient temperature to give a mixture of anhydroluteins, (3R,6'R)-α-cryptoxanthin, and (3R)-β-cryptoxanthin in good yields. In this reaction, lutein is initially converted to anhydroluteins quantitatively and the latter undergoes ionic hydrogenation to give a mixture of (3R,6'R)-α-cryptoxanthin and (3R)-β-cryptoxanthin. Depending on the experimental conditions, 18–34% of anhydroluteins remain unreacted. The invention also demonstrates that an alternative route to these carotenoids is to first convert (3R,3'R, 6'R)-lutein to anhydroluteins with an acid and then in a subsequent step react the resulting products with TFA/$Et_3SiH$ to obtain (3R,6'R)-α-cryptoxanthin and (3R)-β-cryptoxanthin. The invention also demonstrates that the mixture of carotenoids obtained from these reactions can be subjected to column chromatography to separate and purify three major fractions consisting of 1) a mixture of (3R,6'R)-α-cryptoxanthin and (3R)-β-cryptoxanthin, 2) a mixture of anhydroluteins, and 3) (3R,3'R)-zeaxanthin.

This invention further demonstrates that (3R,3'R,6'R)-lutein can be converted selectively to (3R,6'R)-α-cryptoxanthin by sodium cyanoborohydride ($NaCNBH_3$) and zinc iodide ($ZnI_2$) or zinc bromide ($ZnBr_2$) in halogenated solvents (dichloromethane, 1,2-dichloromethane) or tert-butyl methyl ether at ambient temperature within 1–5 h, in yields of up to 90%.

To avoid the use of toxic sodium borohydride and chlorinated solvents, this invention further demonstrates that (3R,3'R,6'R)-lutein can be converted selectively to (3R,6'R)-α-cryptoxanthin by borane-trimethylamine or borane-dimethylamine complexes in the presence of aluminum chloride in THF or 1,2-dimethoxyethane at ambient temperature within 1–2 h, in yields of up to 90%.

Alternatively, this invention demonstrates that in preferred embodiments, lutein undergoes selective allylic deoxygenation by treatment with a 3.0 M solution of lithium perchlorate-diethyl ether at ambient temperature to give a mixture of mostly anhydrolutein I and (3R,61R)-α-cryptoxanthin.

The commercially available lutein is isolated from extracts of marigold flowers and contains approximately 5–7% zeaxanthin. Because zeaxanthin does not react with TFA/$Et_3SiH$ or $NaCNBH_3$/$ZnI_2$ or $NaCNBH_3$/$ZnBr_2$ or $Me_3N.BH_3$/$AlCl_3$ or $Me_2NH.BH_3$/$AlCl_3$ or lithium perchlorate-diethyl ether, it can be fully recovered in the final product.

From the foregoing description, one skilled in the art can easily ascertain the essential characteristics of this invention, and without departing from the spirit and scope thereof, can make various changes and modifications of the invention to adapt it to various uses and conditions without undue experimentation. All patents, patent applications and publications cited herein are incorporated by reference in their entirety.

What is claimed is:

1. A process for converting (3R,3'R,6'R)-lutein to a mixture of anhydroluteins I, II, III, (3R,6'R)-α-cryptoxanthin and (3R)-β-cryptoxanthin, comprising reacting (3R,3'R, 6'R)-lutein in the presence of a strong acid and a hydride ion donor in a chlorinated solvent or toluene under an inert atmosphere to give a mixture of anhydroluteins I, II, III, (3R,6'R)-α-cryptoxanthin and (3R)-β-cryptoxanthin.

2. The method of claim 1, wherein said (3R,3'R,6'R)-lutein comprises 85% total carotenoids.

3. The method of claim 1, wherein said (3R,3'R,6'R)-lutein contains greater than 97% total carotenoids.

4. The method of claim 1, wherein said (3R,3'R,6'R)-lutein comprises about 5–7% (3R,3'R)-zeaxanthin.

5. The method of claim 1, wherein the strong acid is trifluoroacetic acid (TFA).

6. The method of claim 1, wherein the hydride ion donor is triethylsilane ($Et_3SiH$).

7. The method of claim 1, wherein the chlorinated solvent is dichloromethane or 1,2-dichloroethane.

8. The method of claim 1, wherein one mole equivalent of (3R,3'R,6'R)-lutein, containing about 5–7% (3R,3'R)-zeaxanthin in a chlorinated solvent is stirred with about 2–3 equivalent of $Et_3SiH$ and about 3.0–3.5 equivalent of TEA at ambient temperature for about 5–10 hours under an inert atmosphere.

9. The method of claim 8, wherein the mixture of anhydroluteins I, II, III, (3R,6'R)-α-cryptoxanthin, and (3R)-β-cryptoxanthin is isolated by neutralizing the strong acid with a base and displacing the chlorinated solvent with a higher boiling alcohol by distillation until carotenoids crystallize from the aqueous alcohol.

10. The method of claim 9, farther comprising collecting the crystalline carotenoids, washing with acetone or alcohol, and drying under high vacuum at about 40–60° C.

11. The method of claim 10, wherein the crystalline carotenoids are washed at ambient temperature or 0° C. to −20° C. with a $C_5$–$C_7$-hydrocarbon solvent or petroleum ether to remove the Z(cis)-carotenoids and give a crystalline mixture of all-E(trans)-carotenoids enriched in recovered (3R,3'R)-zeaxanthin.

12. The method of claim 10, wherein the crystalline carotenoids are subjected to column chromatography employing a hydrocarbon solvent in combination with acetone or methyl ethyl ketone, ethyl acetate, a $C_4$–$C_6$-ether or mixtures thereof to obtain a pure mixture of (3R,6'R)-α-cryptoxanthin and (3R)-β-cryptoxanthin, a separate mixture of anhydroluteins I, II, III, and pure (3R,3'R)-zeaxanthin.

13. The method of claim 12, wherein the hydrocarbon solvent is pentane, hexane, heptane, or petroleum ether and $C_4$–$C_6$-ethers are diethyl ether, diisopropyl ether, tert-butyl methyl ether, 1,2-dimethoxyethane, or THF.

14. The method of claim 1, wherein (a) (3R,3'R,6'R)-lutein (85% total carotenoids) or (b) purified lutein (greater than 97% total carotenoids) containing about 5–7% (3R, 3'R)-zeaxanthin or mixtures of (a) and (b) is first converted to a mixture of anhydroluteins and this product is then allowed to react with a strong acid and a hydride ion donor in a chlorinated solvent or toluene under an inert atmosphere to give a mixture of unreacted anhydroluteins, (3R,6'R)-α-cryptoxanthin, (3R)-β-cryptoxanthin and recovered (3R, 3'R)-zeaxanthin.

15. A process for converting (a) (3R,3'R,6'R)-lutein (85% total carotenoids) or (b) purified lutein (greater than 97% total carotenoids) containing 5–7% (3R,3'R)-zeaxanthin or mixtures of (a) and (b) to a mixture of anhydroluteins I, I, III, comprising reacting (3R,3'R,6'R)-lutein with an acid selected from the group consisting of TFA and boron trifluoride, or an aqueous mineral acid in a solvent at ambient temperature to give a mixture of anhydroluteins and the recovered (3R,3'R)-zeaxanthin.

16. The process of claim 15, wherein said aqueous mineral acid is aqueous sulfuric acid, aqueous hydrochloric acid or aqueous phosphoric acid; said solvent is dichloromethane, 1,2-dichloroethane, tetrahydrofuran, tert-butyl methyl ether, toluene, or a $C_1$–$C_4$ alcohol.

17. The method of claim 14, wherein the strong acid is TFA.

18. The method of claim 14, wherein the hydride ion donor is $Et_3SiH$.

19. The method of claim 14, wherein the solvent is dichloromethane, 1,2-dichloroethane or toluene.

20. The method of claim 14, wherein one mole equivalent of anhydroluteins I, II, and III, containing 6–10% (3R,3'R)-zeaxanthin in a chlorinated solvent or toluene is stirred with about 2.8–3 equivalent of $Et_3SiH$ and about 3.8–12 equivalent of TFA at ambient temperature for about 2.5–6 hours under an inert atmosphere to give a mixture of unreacted anhydroluteins, (3R,6'R)-α-cryptoxanthin, (3R)-β-cryptoxanthin and recovered (3R,3'R)-zeaxanthin.

21. The method of claim 20, wherein the product mixture is worked up by neutralizing the acid with an aqueous or an organic base and displacing the chlorinated solvent or toluene with a higher boiling alcohol by distillation under reduced pressure until carotenoids crystallize from the aqueous alcohol.

22. The method of claim 21, wherein the crystalline carotenoids are collected and washed with acetone or alcohol and dried under high vacuum at 40–60° C.

23. The method of claim 21, wherein the crystalline product is washed at ambient temperature or 0° C. to −20° C. with a $C_5$–$C_7$-hydrocarbon solvent or petroleum ether to remove the Z(cis)-carotenoids and yield a crystalline mixture of all-E(trans)-carotenoids enriched in recovered (3R, 3'R)-zeaxanthin.

24. A process for converting (a) (3R,3'R,6'R)-lutein (85% total carotenoids) or (b) purified lutein (greater than 97% total carotenoids) containing 5–7% (3R,3'R)-zeaxanthin or mixtures thereof to (3R,6'R)-α-cryptoxanthin, comprising reacting (3R,3'R,6'R)-lutein with a zinc halide and sodium cyanoborohydride in a chlorinated solvent or an ether at ambient temperature under an inert atmosphere to give (3R,6'R)-α-cryptoxanthin and recovered (3R,3'R)-zeaxanthin.

25. The method of claim 24, wherein the chlorinated solvent is dichloromethane or 1,2-dichloroethane and the ether is tert-butyl methyl ether (TBME).

26. The method of claim 24, wherein one mole equivalent of (3R,3'R,6'R)-lutein containing 5–7% (3R,3'R)-zeaxanthin in a chlorinated solvent or TBME is stirred with 7.5 equivalent of $NaCNBH_3$ and 4.0 equivalent of zinc iodide or zinc bromide at ambient temperature for about 1–5 hours under an inert atmosphere to give (3R,6'R)-α-cryptoxanthin and recovered (3R,3'R)-zeaxanthin.

27. The method of claim 26, wherein the product is worked up by filtering the crude mixture of (3R,6'R)-α-cryptoxanthin and (3R,3'R)-zeaxanthin and evaporating the chlorinated solvent or TBME under reduced pressure by displacement with a higher boiling alcohol until carotenoids crystallize out.

28. The method of claim 27, wherein the crystallized carotenoids are collected by centrifugation or filtration and are washed with alcohol or acetone.

29. The method of claim 28, further comprising drying the crystals under high vacuum at 60° C. to obtain a mixture of recovered (3R,3'R)-zeaxanthin and (3R,6'R)-α-cryptoxanthin.

30. A process for converting (a) (3R,3'R,6'R)-lutein (85% total carotenoids) or (b) purified lutein (greater than 97% total carotenoids) containing 5–7% (3R,3'R)-zeaxanthin or mixtures thereof to (3R,6'R)-α-cryptoxanthin, comprising reacting (3R,3'R,6'R)-lutein with borane-trimethylamine or borane-dimethylamine complex in the presence of aluminum chloride in a first solvent at ambient temperature under an inert atmosphere to give (3R,6'R)-α-cryptoxanthin and recovered (3R,3'R)-zeaxanthin, wherein said first solvent is an ether.

31. The method of claim 30, wherein said ether is tetrahydrofuran or 1,2-dimethoxyethane.

32. The method of claim 30, wherein one mole equivalent of (3R,3'R,6'R)-lutein containing 5–7% (3R,3'R)-zeaxanthin in an ether is stirred with about 6 mole equivalent of borane-trimethylamine or borane-dimethylamine complex in the presence of about 2.3 mole equivalent of aluminum chloride at ambient temperature for about 1–2 hours under an inert atmosphere to give (3R,6'R)-α-cryptoxanthin and recovered (3R,3'R)-zeaxanthin.

33. The method of claim 32, wherein the (3R,6'R)-α-cryptoxanthin and recovered (3R,3'R)-zeaxanthin is isolated by partitioning into an aqueous solution of sodium bicarbonate, separating resulting organic layer, and evaporating the solvent until a mixture of (3R,6'R)-α-cryptoxanthin and unreacted (3R,3'R)-zeaxanthin crystallizes.

34. The method of claim 33, wherein the first solvent is THF and a second solvent selected from the group consisting of ethylacetate and a $C_4$–$C_6$-ether is added together with the aqueous sodium bicarbonate before the organic layer is separated.

35. The method of claim 33, wherein the crystallized mixture is collected by centrifugation or filtration and is washed with an alcohol or acetone.

36. The method of claim 35, further comprising drying the washed crystallized mixture under high vacuum at 60° C. to obtain a mixture of recovered (3R,3'R)-zeaxanthin and (3R, 6'R)-α-cryptoxanthin.

37. A process for converting (a) (3R,3'R,6'R)-lutein (85% total carotenoids) or (b) purified lutein (greater than 97% total carotenoids) containing 5–7% (3R,3'R)-zeaxanthin or a mixture of (a) and (b) to a mixture of anhydrolutein I and (3R,6'R)-α-cryptoxanthin, comprising reacting (3R,3'R, 6'R)-lutein with an ether solution of lithium perchlorate in the presence of a hydride ion donor at ambient temperature under an inert atmosphere to give a mixture of anhydrolutein I, (3R,6'R)-α-cryptoxanthin, and recovered (3R,3'R)-zeaxanthin.

38. The method of claim 37, wherein the hydride ion donor is $Et_3SiH$.

39. The method of claim 37, wherein the ether is ethyl ether, isopropyl ether or TBME.

40. A method for converting (3R,3'R,6'R)-lutein to a mixture of anhydrolutein I and (3R,6'R)-α-cryptoxanthin, comprising reacting said (3R,3'R,6'R)-lutein with lithium perchlorate and a hydride ion donor in an organic solvent.

41. A method for converting (3R,3'R,6'R)-lutein to a mixture of anhydrolutein I and (3R,6'R)-α-cryptoxanthin, comprising reacting one mole equivalent of lutein, containing 5–7% (3R,3'R)-zeaxanthin in diethyl ether with 167 mole equivalent of lithium perchlorate in the presence of 3.5–4.0 mole equivalent of $Et_3SiH$ at ambient temperature under an inert atmosphere overnight to give a mixture of anhydrolutein I, (3R,6'R)-α-cryptoxanthin, and recovered (3R,3'R)-zeaxanthin.

42. The method of claim 41, wherein the product mixture of anhydrolutein I, (3R,6'R)-α-cryptoxanthin and recovered (3R,3'R)-zeaxanthin is isolated by addition of water, separating the organic layer, and displacing the ether with a higher boiling hydrocarbon or alcohol by distillation until carotenoids crystallize out.

43. The method of claim 42, wherein the crystals are removed by filtration or by centrifugation.

44. The method of claim 43, fierier comprising drying the crystalline carotenoids under high vacuum at 60° C. to give a mixture of anhydrolutein I, (3R,6'R)-α-cryptoxanthin, and recovered (3R,3'R)-zeaxanthin.

45. A process for converting (a) (3R,3'R,6'R)-lutein (85% total carotenoids) or i(b) purified lutein (greater than 97% total carotenoids) containing 5–7% (3R,3'R)-zeaxanthin or mixtures thereof to (3R,6'R)-α-cryptoxanthin, comprising reacting (3R,3'R,6'R)-lutein with zinc bromide or iodide and sodium (trifluoroacetoxy)borohydride in a chlorinated solvent under an inert atmosphere to give (3R,6'R)-α-cryptoxanthin and recovered (3R,3'R)-zeaxanthin.

46. The method of claim 45, wherein the chlorinated solvent is dichloromethane or 1,2-dichloroethane.

47. The method of claim 45, wherein the reaction is carried out at about 0–5° C.

48. The method of claim 45, wherein about 1.3 mole equivalents of zinc bromide or iodide, and about 4 mole equivalents of sodium (trifluoroacetoxy)-borohydride are reacted at 0° C. for up to about 5 hours to give a crude product.

49. The method of claim 48, wherein an aqueous solution of sodium bicarbonate is added to the crude product, the resulting organic layer is separated and then dried.

50. The method of claim 49, wherein the dried organic layer is evaporated by gradual displacement with a higher boiling alcohol until (3R,6'R)-α-cryptoxanthin crystallizes.

51. The method of claim 50, wherein the crystallized (3R,6'R)-α-cryptoxanthin is collected and the crystals are washed with an alcohol or acetone.

52. The method of claim 51, wherein the washed crystals are dried under vacuum.

* * * * *